United States Patent [19]
Yaver et al.

[11] Patent Number: 6,008,029
[45] Date of Patent: *Dec. 28, 1999

[54] PURIFIED COPRINUS LACCASES AND NUCLEIC ACIDS ENCODING THE SAME

[75] Inventors: Debbie Sue Yaver, Davis; Kimberley M. Brown, Elk Grove, both of Calif.; Sakari Kauppinen, Copenhagen; Torben Halkier, Frederiksberg, both of Denmark

[73] Assignee: Novo Nordisk Biotech Inc., Davis, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/689,421

[22] Filed: Aug. 9, 1996

Related U.S. Application Data

[60] Provisional application No. 60/002,800, Aug. 25, 1995.
[51] Int. Cl.$^6$ .............................. C12N 9/02; C12N 1/20; C12N 1/14; C12N 15/00
[52] U.S. Cl. ................ 435/189; 435/252.3; 435/254.11; 435/320.1; 435/325; 435/410; 536/23.2
[58] Field of Search ............................... 536/23.1, 24.32, 536/23.2; 435/183, 320.1, 252.3, 189, 254.11, 410, 325; 530/324; 935/1, 22, 66

[56] References Cited

U.S. PATENT DOCUMENTS 5,200,313  4/1993  Carrico ......................................... 435/6

FOREIGN PATENT DOCUMENTS

| JO 2005877 | 1/1990 | Japan | C12N 15/53 |
| JO 2027986 | 1/1990 | Japan | C12N 12/53 |
| WO 92/01046 | 1/1992 | WIPO | C12N 9/02 |
| WO 95/07988 | 3/1995 | WIPO | C12N 15/53 |
| WO 96/00290 | 1/1996 | WIPO . | |
| WO 96/06930 | 3/1996 | WIPO . | |

OTHER PUBLICATIONS

Giardina et al., "The Gene, Protein and Glycam Structures of Laccase from Pleurotus Ostreatus", Eur. J. Biochem 235., pp. 508–515, 1996.

Kojima et al., "Cloning, Sequence Analysis, and Expression of Ligninolytic Phenoloxidase Genes of the White–Rot Basidiomycete Coriolus", The Journal of Biological Chemistry, Inc., vol. 265, No. 25, (1990) 15224–15230.

Kim et al., "Selection of Laccase Over–Secreting Mutant in Coprinus Congregatus", Jun. 1995, pp. 146–148.

Saloheimo et al. (1991) J. Gen. Microbiol. 137:1537–44.

Germann et al. (1988) J. Biol. Chem. 263:885–896.

*Primary Examiner*—Bradley Sisson
*Assistant Examiner*—Einar Stole
*Attorney, Agent, or Firm*—Steve T. Zelson; Elias Lambiris; Robert L. Starnes

[57] ABSTRACT

The present invention relates to polypeptides having laccase activity and isolated nucleic acid sequences encoding the polypeptides. The invention also relates to nucleic acid constructs, vectors, and host cells comprising the nucleic acid sequences as well as methods for producing the polypeptides.

17 Claims, 11 Drawing Sheets

```
CAACGTCAAACGGCGAAAACCGTCTATCAGGGCGATGCCCACTACGTGAACCATCACCCTAATCAAGTTTTTGGGCTCGAGTGCCGTAAAGCACTA      100
AATCGGAACCCTAAAGGGAGCCCCCGATTTAGAGCTTGACGGGAAGCTTGAACCTGGCGAGAAACCCGGCGAAAGGAAGAAGCGAAAGGAGCGGGCTA    200
GGGCGCTGCCAAGTGTAGGCGGTGTCACGGCTGCCGTGCCGGCCCTCTCGCTATTACGCCAGGCCGCGCCTTAATGCCGCTACAGGGCGCGTCCATTCAGGCTGCC  300
CAACTGTTGGGAAGGCGCGATCGGTGCGGGCCCTCTCGCTATTACGCCAGGCTGCCAAGGGGATGGTGCAAGGGGATGTGCTGCAAGGGATGTGCTGCAGGCAGCG  400
TTTCCAGTCACGACGTGTAAAACGACGGCCAGTGAATTGAATTTAGGTGACACTATAGAAGAGCTATGACGTCCAATGCATGCACCGTACGTAAGCTTGG      500
ATCCTCTAGAGCGACCCCGACTAGTGACCTCGTCGACCGGGAATTGCAGCTCGTCTATCTCCGCTCTCTCTCCACAGACTCTCCTTGACAGCCT          600
AAAATCTGTATGAAGTTGGCGAAGAAACCTCAGACTACTCGTCGAAGAAACCTCAGACTACTCGTGCCAAGGCTCAGATCGTCAATTCGTCGAT         700
CGTCGTATCAGAGAGAACAGAACAACAATGTCAAGAACGTCAGTCCCGACGGTTTCACTCGAGCGtaagtataggtcttcagcacactgttgattatcattacttactlaccaactt  800
                                         M  F  K  N  L  L  S  F  A  L  L  A  I  S  V  A  N  A  Q  I  Y  H  S  V  D  900
ACCATGACCCTCACCAACGCGAACGTCAGTCCCGACGGTTTCACTCGAGCGTACGTTCGCACACTGTCAACGACACTGCATCATCATCATACCATCTGGACAACCCA        1000
  I  M  I  L  T  H  A  N  Y  S  P  D  G  F  I  R  A
aacagTGGTATCCTCGCAGAGTTCATGGACTCTTATTCGAGGTCGAAAGACAACTTCAGCTCAACGTCTTAACGACTTGGACAACCCCA           1000
                                                                                               G  I  L  Y  N  G  Y  H  G  P  L  I  R  G  G  K  N  D  N  F  E  L  H  Y  N  D  L  D  N  P
CTATGCTTCGGCCTACCAGTATCGtgagttctacagaaataaacactgatcatcatgatccagaacactgacaacgttctgatttttggtttgcttgtag   1100
  T  M  L  R  P  T  S  I
CATTGGCACGGTCTCTCTTCCAACGAGGACCAACTGGGCTGATGGTGCAGATGGTCAACGATGCCGGATCTCTCCAGGCCATGCTTTCCTCTACAAGT       1200
  M  V  H  G  L  F  Q  R  G  T  N  W  A  D  G  A  D  G  Y  N  Q  C  P  I  S  P  G  H  A  F  L  Y  K
TCACTCCAGCTGCACGGCTGGTACTTCTGTACCATTCCCCACTTTGgtaagccccgaccccggctatgatcatcttgactgggtcctgattgatgt         1300
  F  I  P  A  G  M  A  G  I  F  W  Y  H  S  H  F
ccaactaatttactagGCACCCAATACTGCGATGGTCTCCGTGTCCAATGCTCATTACGACGACAATGACCACACGCTGCCCTCTACGACGAGGATG         1400
                  G  T  Q  Y  C  D  G  L  R  G  P  M  Y  I  Y  D  D  H  D  P  H  A  A  L  Y  D  E  D
ACGAGAACACCATCATTACCCTCGCCGATTGGTACCATATCCCCGCCAGCTGCTGCCCAGGTGCTGCTGCCCAGTGCTACGCTCATCAACGTAAGG         1500
  D  E  M  T  I  I  T  L  A  D  W  Y  H  I  P  A  P  S  I  Q  G  A  A  Q  P  D  A  T  L  I  H  G  K  G
TCGCTACGTGGGGCCCAGCTGCCGAGTTCGATCGTCAATGTCGAGCAAGGAAGTACCAATGCGTTGATCTCGGTCGTCGCCACCCCAAC           1600
  R  Y  G  G  P  A  A  E  L  S  I  Y  N  Y  E  Q  G  K  K  Y  R  M  R  L  I  S  L  S  C  D  P  N
TGGCAGTTCTCCATTGACGGACATGAGTTCACTGATAGAGTTCTCGAGTGCTCTACTGTCGATGTCGGCCATACGTTCAGCGCATCTTCACTGgta        1700
  W  Q  F  S  I  D  G  H  E  L  T  I  I  E  Y  D  G  Q  L  T  E  P  H  T  Y  D  R  L  Q  I  F  T
```

FIG. 1A

```
agcattgaaatcggtgtgttccgttgagaagcacactcaccttta atcagGTCAAAGGTACTCCTTCGTTCTCGACGCAACCAGCCGTGACAACT    1800
                                              G  Q  R  Y  S  F  Y  L  D  A  H  Q  P  Y  D  H
ACTGGATCCGTGCCTCAACCAGAACAAGGGTCGAAACCGACTTGCTGTCAACTCCTGTCAACTCCTTCGCTATGCCGGGCCTGCCAA                          1900
 T  W  I  R  A  Q  P  H  K  G  R  N  G  L  A  G  T  F  A  N  G  Y  N  S  A  I  L  R  Y  A  G  A  A  N
CGCTGATCCAACCACTCCGCCAACCCGGCCAACCCGACCTCCATGCTCTCATCGACCCGGCTGCTCCCGTATCCCACTCCG                               2000
 A  D  P  T  T  S  A  H  P  H  P  A  Q  L  N  E  A  D  L  H  A  L  I  D  P  A  A  P  G  I  P  T  P
GGGCCTGCAGAGCTCAACCTCCGATTCAATTGGGCTTCAGCGGGTCGGCCTTCAGCGATTCACGATTAACGAACCCATACGAGACTCCAACCGTTCCTACCCTCT        2100
 G  A  D  Y  H  L  A  F  Q  L  G  F  S  G  G  R  F  T  I  N  G  T  A  Y  E  S  P  S  Y  P  T  L
TGCAGATTATGAGTGGCAGAGTCGGAACGACTGCTCCCTGCTGGAACCTGTATGAGTGGCAGGAACCAAGTGTTGAGCTTGTTGTCCTGC                      2200
 L  Q  I  M  S  G  A  Q  S  A  M  D  L  L  P  A  G  S  Y  Y  E  L  P  R  H  Q  Y  Y  E  L  Y  Y  P  A
TGGTGTCTCCGGTGGTCCTCCATCCTTTCCATCGtgtacgtcaagttttctttctcttttttcatggtggtcaagtgtacatgagctta                      2300
 G  Y  L  G  G  P  H  P  F  H  L  H  G
ccaaggattgaattgtgtagCATGGTCTTCAGTCGTTCAGTCGTCCAGGAGTGCAGGCAGCACTACAACTTGTCAACCCGTCAAGCCCATGTTGTTAGTCT          2400
                     H  A  F  S  Y  Y  R  S  A  G  S  S  T  Y  M  F  V  H  P  Y  K  R  D  Y  Y  S  L
TGGTGTTACTGGAGACGAAGTTACCATTCGXTTCGTCACGGATAACCCAGGCCCGTGGTTCCATGCCACATTGAATTCCATCTCATGAAgtaagtc              2500
 V  H  P  Y  K  R  D  Y  Y  S  L
                                H  H  I  E  F  H  L  M  N
                                                          G  Y  T  G  D  C  Y  T  I  R  F  Y  T  D  N  P  G  P  W  F  F  H  C  H  I  E  F  H  L  M  N
ttcatatccatcgttgtatactccaggtctaaccccctccacagCGGCTTGCCAGCTCTTTGCTGAAGACATGGCAACACGTTGATGCTAACAA              2600
                                              G  L  A  I  Y  F  A  E  D  M  A  H  T  Y  D  A  H  H
CCCCACCTGgtacgtccccctcctgtcttgactcaaatactaatttccgaagctaacttcggcatcaattacgTCGAGTGGGCCCAGTTTGCCGAGATTTACG        2700
 P  P                                                                      Y  E  W  A  Q  L  C  E  I  T
ATGACCTGCCGCCTGAGGCCACTTCAAACCGTTGTGCTGCGCCTGCGCGCTGCCTATGCCGGCTGAGCCCACGGCTTTCGGCCAAGTTCCGCCAGGAGGGCTTGTAGATAAT  2800
 D  D  L  P  P  E  A  T  S  Y  Y  R  R  A  E  P  T  G  F  S  A  K  F  R  R  E  G  L
ATTATAGTTGACCAGACGGGCCAGTGCTGTAGGAGCTGTACATACTTATTAACATCGTATGTACTGCCTTTCCCAGAGAAGAGTAGTCCAGAGAAGACAATGTATTGATTGTCGAGTTG  2900
TTATTCATCGTGTGTTATTTATCGGTGTTGTACATATCTATTAACATCGTATGTACTGCCTTTCCCGACCTGCCTTTCCGACCTGTACACCTTTGATTGAATGACAATGAATATCGTCGAGTTG  3000
GAATCCTTGTTGAAGTGCTAGTAAACCTTTTGATGGACTCGAGGCGTACCGGTACCTGCGGATGCACTTCCTCGATTGAATATTGAAGCCGAGGCACGAATCGAA                    3100
CCCACCACCCCGAATGCAAAGTCCAAATCCGGACGGTACCGCAGGCCGACCGTACCTGCAGGCGACCTTGCCGTAACTATATTAGAGCTTGGCCTAATCATGGTCATA                  3200
GCTGTTTCCTGTGTGAAATTGTTATCCGCTCACAACAATTCCACAACATAAAGTGAAGCCGAGCCCGAAGCATAAAGTGAAGCCTGGGGTGCCTAATGAGTGAGCTAA               3300
CTCACATTAATTGCGTTGCGCTCACTG    3327
```

```
CAGCCCGGAAAGCGCTACGCGCTTCCGCCTCGTCTCCCTTTCGTGCGACCCTAACTATGTATTCTCTATTGACGGTCACACCATGgttcgtaccctccc   1700
        S   R   G   K   R   Y   R   F   R   L   V   S   L   S   C   D   P   N   Y   V   F   S   I   D   G   H   T   M
ataatccactcctccctgcctcatatttacgttttgcgactgttagACGGTCATTGAAGTCGATGGTGTCAACCATGAACCGTTGGTTGTCGACCACA   1800
                                                T   V   I   E   V   D   G   V   N   H   E   P   L   V   V   D   H
TTCAAATCTTTGCTGCTCAACGGTACTCGTTTGTCTTGTCTTGAACGCCATCTGGGTCAGGGCTAACCCCAACTACTGGGTCTAACCCCAACCTCGGCTCTGTCCG   1900
  I   Q   I   F   A   G   Q   R   Y   S   F   V   L   N   A   N   R   P   V   N   N   Y   W   V   R   A   N   P   N   L   G   S   V   G
CTTCGGTGGCGGTATTAATTCCGGATATGTGGACCTCCTGCCGCTCGACCTGGATATCTTGTCCACGTCTCAA   2000
  F   G   G   I   N   S   A   I   L   R   Y   V   G   A   P   A   V   D   P   T   T   S   Q   L   P   F   S   N   P   L   L   E
ACCAACTTGCACCCTCTCGTAAATCCTGCTGCACCGGGTCCCTCCGGTCCTGGTGACGTCGCCATCAACCTGATAATCTTGTCCACGTCTCAA   2100
  T   N   L   H   P   L   V   N   P   A   A   P   G   G   P   S   P   G   D   V   D   V   A   I   N   L   D   I   L   F   D   V   S
TCCTCAAGTTCACTGTCAACGGTGCTACTTTCGATGAACAAGGTCACTATTCCGGTGGTATCGGTCTCCGtgagtcttttcttcttcatcttc   2200
  S   L   K   F   V   N   G   A   T   F   D   E   P   P   V   P   L   L   Q   I   L   S   G   A   H   T   A   S   S   L   L   P
CTCTGGCAGCCTCTACACTCTTCCCCTAACAAGGTCATTGAGCTCACTATTCCGGGTGGTATCGGTCTCCGtgagtcttttcttcttcatcttc   2300
  S   G   S   V   Y   T   L   P   P   N   K   V   I   E   L   T   I   P   G   G   I   G   A   P
tctcgatctcgatggtgttcactcactgttgaaaccagCACCCCCATCTTCACGgtggtatccatccgttaagttcattaagtcccatgctg   2400
                                        H   P   I   H   L   H   G
accgtttgacagCATACCTTCAAGGTTGTCCGTAGCCGCAGGCAGCTCGACTTACAACTTCGTCAATCCGTTGAGCGGAGATGTGTCAACGTTGGTCAAG   2500
              H   T   F   K   V   V   R   S   A   G   S   S   T   Y   N   F   V   N   P   V   E   R   D   V   V   N   V   G
CTGGCCGACAATGTCACCATTCGATTCGTCACTGATAATGCTGGTCCTGGATTCTTCACTgtgccgtatttcttttaggcattcaacgtcagggtctt   2600
  A   G   D   N   V   T   I   R   F   V   T   D   N   A   G   P   W   I   L   H   C
acccccgttcttttcagCCACATTGGCCATTGTTTtgtaagttcacgtttgacgcatcaggcgaatggtactctaacttcctccaGGGGCCCTGT   2700
                    H   I   D   W   H   L   V   L                                                           G   L
CTGTCGTCTTCGCGGAAGATGTCCCCACCATCGATAGCTCCGTTCAACCTgtaagttctgcgtgcctctgctcgatatcatttggcttcttggct   2800
  S   V   V   F   A   E   D   V   P   T   I   D   S   S   V   Q   P
ttagCGGCCCTGGCATGATCGTGCCCATCTATGACGCTCTTCCCCCGGCAGGTAATCTCGCCACGAGGTAAATCTCGGCACGGTATGACTGGACAGG   2900
      P   A   W   H   D   L   C   P   I   Y   D   A   L   P   P   G   T   R
TTACGGAAATCAAAGTAAATGTTGGATAAGAAGAATAACA   2940
```

```
TTCCGCCTTGTTCCCTTTCATCGATCCTAATTATGTATTCTCTATCGATGGCATACCATgtacgcactagtccatccctgtaaacgggtgcta  1600
 F  R  L  V  S  L  S  C  D  P  N  Y  V  F  S  I  D  G  H  T  M
acgacgtgtatcatccttagACTGTTATTGAGGTCGACGGAGTTAACGTCCAACCTCTCGTTGCGACTCGATCCAGATCTTCCAGGTCAGGCTACT  1700
                       T  V  I  E  V  D  G  V  N  V  Q  P  L  V  V  D  S  I  Q  I  F  A  G  Q  R  Y
CGTTCGTTCTCAACGCCAACCCCGTCGGCAACTACTGGTCGCAGCCAACATCGTACGGCCTTCGTCGTGGAGTCAATTCTGCGAT  1800
 S  F  V  L  N  A  N  R  P  V  G  N  Y  W  V  R  A  N  P  N  I  G  T  T  G  F  V  G  G  V  N  S  A  I
TCTGCGCTATGTGGGCGCCTCCAATACAGACCCCACTACCCCCAAATCTCTTTCAGCAACCCTCTCCTTGAGACCAATCTCCACCCTTGACCAACCCT  1900
 L  R  Y  V  G  A  S  N  T  D  P  T  T  Q  T  P  F  S  N  P  L  L  E  T  N  L  H  P  L  T  N  P
GCTGCTCGGCTTGCCTACCCCAGGTGGCGTCGACTGCTGCTCTTGCTCTTCAGATTCAGTAGTCCACCTTCTCCCCTTAACGGAGCCA  2000
 A  A  P  G  L  P  T  P  G  G  V  D  V  A  I  N  L  N  T  V  F  D  F  S  S  L  T  F  S  V  N  G  A
CTTTCATCAACCGGCTCCTCCCTCTGTCTTGCTCTTCAGATCATGAGCGGCGCTCAGGCCTGCACAGAGACTCCCAGCAGCTCTCTCCCCGTCTACGTCTTCCCCG  2100
 T  F  H  Q  P  P  V  P  V  L  L  Q  I  M  S  G  A  Q  T  A  Q  Q  L  L  P  S  G  S  V  Y  V  L  P  R
TAACAAAGTCATCGAGCTTTCTATGCCTGGAGGCTCCACTGGCAGTCCCgtaagtctaattgtcttcattcaacaagtcggtgataacgctggatc  2200
 N  K  V  I  E  L  S  M  P  G  G  S  T  G  S  P
attcgctgacagCATCCCTCCATCCCTTCCACCGTGtatgtagcctctctgtctgatctcattcggaagcgttactgacggtgcttcttgttcgatctgat  2300
             H  P  F  H  L  H  G
agCACGAATTGCTCGTGTGGTGAGAAGCCGGGGAGTTCGACTTCGCGAACCCGGTCGACCTACGCCAGGAGATGTCCTGAGTGCCGGTGTTGCTGCTGACAA  2400
             H  E  F  A  V  V  R  S  A  G  S  S  T  Y  N  F  A  N  P  V  R  R  D  V  V  S  A  G  V  A  G  D  N
CGTCACCATTCCGATTCCTACCGATAACCCTGACTTCCCATTGgtgcgtcaagtcatcgtcctcgtgctgaattgattgtcaaccaagata  2500
 V  T  I  R  F  T  D  N  P  G  P  W  I  L  H  C
tcacatactlagCCATATCGACTGGCACTTGTTTgtaagtcttcgttcttccagacgtgattaacttactgatcgatcgatggaatacgGGGG  2600
              H  I  D  W  H  L  V  L                                                              G
TTGGCTGTAGTGTTCGCTGAGGACGCTCCTACTGTTGCAACCATGGATCCCCCTCgtgagtagcgccgtgctgtttgaggagttgtgaacccgagctca  2700
 L  A  V  V  F  A  E  D  A  P  T  V  A  T  M  D  P  P
acgtgaaacgttttccacttacagCTGCTTGGACCAACTTGCCCGATCTACGACGCTCTCCCTCCCAACATAAGTCCTTCAATTCAAGGCTGTTG  2800
                         P  A  W  D  Q  L  C  P  I  Y  D  A  L  P  P  N  T
```

FIG.3B

```
ACCTGAAGGGAGCAACAAGGAAAGTAAGAGAAAGGCAGTCACATCCCGTCGGTTGCCTCTGAAATATCGATTAATCACGCTTTTATCACTTGTAATTA  2900
TCTTTCTTTGTTACAGTGGCTCTTTGACCTGGCTCTGCCTGGCTCTCCAGTGCGTTAGAGTGCGATAATAATAGCAATTCTCTACTTTTAGCCAGATTTTAGGCAGGGC  3000
TGTGGTACGCTTTATATTAAGTTAAAAGAGCACCAATAATGTCGCCCCTCAGCTGGCCTCTGTGCGGCTGGTGGCACTTCCTGTCCTGGACTAGCTCAGTTGGTTAGAGCGTCGTGCTAA  3100
TAACGCGAAGGTCTTGGGTTCGATCCCCACGTGGCCAGTAGCCCCCTTTTTGTTAATCCTGGCACTTCCTGTTCCTACTAACCCTTTTGAGAGTCCAG  3200
AAAAATCACCATGACTTAATTTTTCTTTCATAGAAGTCCTGGAAGGGTAAGGAAGTGATATAACTAGAAGACCAACATTCAGTGCTGGTCGTCAGAT  3300
CGAGGTGTCTTTTCGACCAATCGGGCGAAGCATTCGGCGAAGATTCGATCGCAGCATCTCGAACGCGAAGGACTGTCGAAGAA  3400
CGTTACGTACGCGGATTGTCAGTTTACGAAGGCGAGGAACCCATTGAGAGTAGATCGTCAAGCGTCTTCCATTGGCCCAGGTCCCACATTCAGATCG  3500
CAGCCGATTTGAACGATAGGAATGATATTGAGTCCTCCAGAAGCGTTCTGTCCCTGCATCAAAGCGA  3566
```

FIG.3C

PURIFIED COPRINUS LACCASES AND NUCLEIC ACIDS ENCODING THE SAME

CROSS-REFERENCE TO RELATED APPLICATIONS

This application is a continuation-in-part of U.S. Provisional Application Ser. No. 60/002,800 filed Aug. 25, 1995, which is herein incorporated by reference.

BACKGROUND OF THE INVENTION

1. Field of the Invention

The present invention relates to polypeptides having laccase activity and isolated nucleic acid sequences encoding the polypeptides. The invention also relates to nucleic acid constructs, vectors, and host cells comprising the nucleic acid sequences as well as methods for producing the polypeptides.

2. Description of the Related Art

Laccases (benzenediol:oxygen oxidoreductases) are multi-copper containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, and perfect forms of Rhizoctonia. Laccase exhibits a wide range of substrate specificity, and each different fungal laccase usually differs only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima. A number of these fungal laccases have been isolated, and the genes for several of these have been cloned. For example, Choi et al. (1992, *Mol. Plant-Microbe Interactions* 5: 119–128) describe the molecular characterization and cloning of the gene encoding the laccase of the chestnut blight fungus Cryphonectria parasitica. Kojima et al. (1990, *Journal of Biological Chemistry* 265: 15224–15230; JP 2-238885) provide a description of two allelic forms of the laccase of the white-rot basidiomycete *Coriolus hirsutus*. Germann and Lerch (1985, *Experientia* 41: 801; 1986, *Proceedings of the National Academy of Sciences USA* 83: 8854–8858) have reported the cloning and partial sequencing of the *Neurospora crassa* laccase gene. Saloheimo et al. (1985, *Journal of General Microbiology* 137:1537–1544; WO 92/01046) have disclosed a structural analysis of the laccase gene from the fungus *Phlebia radiata*.

It is an object of the present invention to provide polypeptides having laccase activity and nucleic acid constructs encoding these polypeptides.

SUMMARY OF THE INVENTION

The present invention relates to isolated polypeptides having laccase activity, obtained from a Coprinus strain. The present invention further relates to isolated polypeptides having laccase activity which have: (a) a pH optimum in the range of about 5 to about 9 at 20° C. using syringaldazine as a substrate; and (b) an isoelectric point in the range of about 3.7 to about 4.0. The present invention also relates to isolated polypeptides which have an amino acid sequence which has at least 65% identity with the amino acid sequence set forth in SEQ ID NO:27, SEQ ID NO:29, or SEQ ID NO:33.

The present invention further relates to isolated nucleic acid sequences encoding the polypeptides and to nucleic acid constructs, vectors, and host cells comprising the nucleic acid sequences as well as methods for producing the polypeptides.

BRIEF DESCRIPTION OF THE FIGURES

FIG. 1 illustrates the nucleotide sequence and the deduced amino acid sequence of the *Coprinus cinereus* lcc1 gene.

FIG. 2 illustrates the nucleotide sequence and the deduced amino acid sequence of the *Coprinus cinereus* lcc3 gene.

FIG. 3 illustrates the nucleotide sequence and the deduced amino acid sequence of the *Coprinus cinereus* lcc2 gene.

DETAILED DESCRIPTION OF THE INVENTION

Polypeptides Having Laccase Activity

Figure 4A:
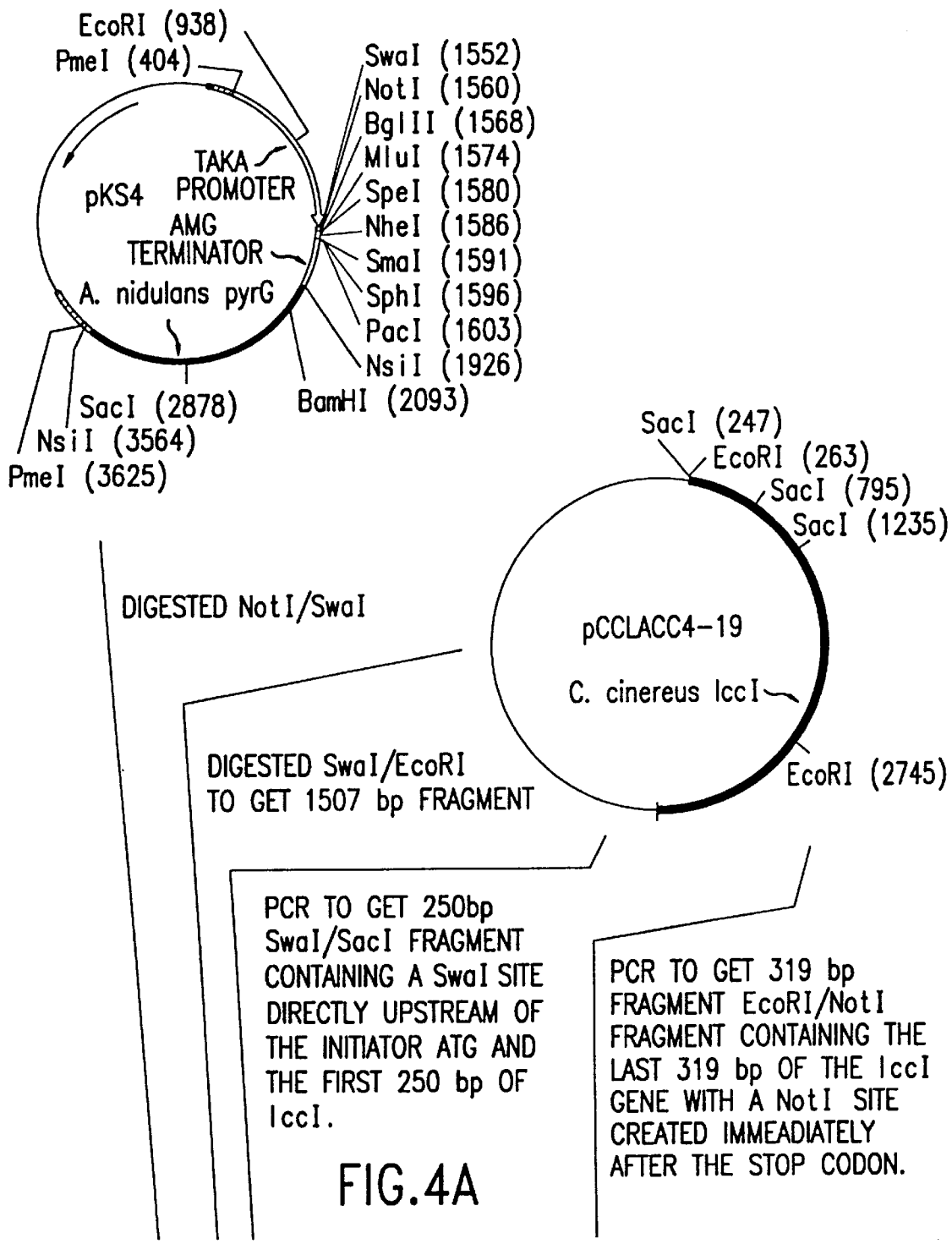
FIG. 4 illustrates the construction of plasmid pDSY67.

The present invention relates to isolated polypeptides having laccase activity (hereinafter "polypeptides"), obtained from a Coprinus strain. The present invention further relates to isolated polypeptides having laccase activity which have:

(a) a pH optimum in the range of about 5 to about 9 at 20° C. using syringaldazine as a substrate; and (b) an isoelectric point in the range of about 3.7 to about 4.0.

The polypeptides preferably have a molecular weight of about 63 kDa (using SDS-PAGE). In another embodiment, the polypeptides are obtained from a strain of the family Coprinaceae, preferably a Coprinus strain, and more preferably a *Coprinus cinereus* strain, e.g., *Coprinus cinereus* IFO 8371 or a mutant strain thereof. In a most preferred embodiment, the polypeptide has the amino acid sequence set forth in SEQ ID NO:27, SEQ ID NO:29, or SEQ ID NO:33.

The present invention also relates to polypeptides obtained from microorganisms which are synonyms of Coprinus as defined by, for example, Webster, 1980, In Introduction to the Fungi, Second Edition, Cambridge University Press, New York. Strains of Coprinus are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL), e.g., from the American Type Culture Collection, ATCC 12890, 36519, 38628, 42727, 48566 (*Coprinus cinereus*); 15744 (*Coprinus clastophyllus*); 12640, 22314 (*Coprinus comatus*); 46457, 46972 (Coprinus congregatus);

48096 (*Coprinus cothurnatus*); 48098 (*Coprinus curtus*); 46973 (*Coprinus disseminatus*); 26829 (*Coprinus domesticus*); 48100 (*Coprinus ephemeroides*); 36567 (*Coprinus fimentarius*); 48097 (*Coprinus gonophyllus*); 20122 (*Coprinus micaceus*); from the Institute for Fermentation (IFO, Osaka, Japan), IFO 8371, 30116 (*Coprinus cinereus*); from Centraalbureau voor Schimmelcultures (CBS; Netherlands) CBS 147.39, 148.39, 175.51 (*Coprinus angulatus*), 147.29 (*Coprinus astramentarius*); 143,39 (*Coprinus auricomus*); 185.52 (*Coprinus callinus*); 159.39, 338.69 (*Coprinus cinereus*); 631.95 (*Coprinus comatus*); 629.95 (*Coprinus friesii*); 627.95 (*Coprinus plicatilis*); 628.95 (*Psathyrella condolleana*); 630.95 (*Panaeolus papilionaceus*) from Deutsche Sammlung von Mikroorganismenn und Zellkulturen (DSM; Germany) DSM 888 (Coprinus radians); 4916 (*Csprinus xanthothrix*); 3341 (*Coprinus sterquilinius*). The invention also embraces polypeptides having laccase activity of other fungi and other members of the family Coprinaceae, for example, laccases from the genera Podaxis, Montagnea, Macrometrula, Psathyrella, Panaeolina, Panaeolus, Copelandia, Anellaria, Limnoperdon, Panaelopsis, and Polyplocium.

For purposes of the present invention, the term "obtained from" as used herein in connection with a given source shall mean that the polypeptide is produced by the source or by a cell in which a gene from the source has been inserted.

The present invention also relates to polypeptides which are encoded by nucleic acid sequences which are capable of hybridizing under standard conditions with an oligonucleotide probe which hybridizes under the same conditions with the nucleic acid sequence set forth in SEQ ID NO:26, SEQ ID NO:28, SEQ ID NO:32 as well as a complementary strand thereof or a subsequence thereof (J. Sambrook, E. F. Fritsch, and T. Maniatus, 1989, *Molecular Cloning, A Laboratory Manual,* 2d edition, Cold Spring Harbor, N.Y.). Hybridization indicates that the analogous nucleic acid sequence hybridizes to the oligonucleotide probe corresponding to the polypeptide encoding part of the nucleic acid sequence shown in SEQ ID NO:26, SEQ ID NO:28, SEQ ID NO:32, or a subsequence thereof, under medium to high stringency conditions (for example, prehybridization and hybridization at 42° C. in 5× SSPE, 0.3% SDS, 200 $\mu$g/ml sheared and denatured salmon sperm DNA, and either 35 or 50% formamide for medium and high stringencies, respectively), following standard Southern blotting procedures.

The nucleic acid sequences set forth in SEQ ID NO:26, SEQ ID NO:28, SEQ ID NO:32, or subsequences thereof may be used to identify and clone DNA encoding laccases from other strains of different genera or species according to methods well known in the art. Thus, a genomic or cDNA library prepared from such other organisms may be screened for DNA which hybridizes with SEQ ID NO:26, SEQ ID NO:28, SEQ ID NO:32, or subsequences thereof. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which are homologous with SEQ ID NO:26, SEQ ID NO:28, SEQ ID NO:32, or subsequences thereof, the carrier material is used in a Southern blot in which the carrier material is finally washed three times for 30 minutes each using 0.2× SSC, 0.1% SDS at 40° C., more preferably not higher than 45° C., more preferably not higher than 50° C., more preferably not higher than 55° C., even more preferably not higher than 60° C., especially not higher than 65° C. Molecules to which the oligonucleotide probe hybridizes under these conditions are detected using an X-ray film.

The present invention also relates to polypeptides which have an amino acid sequence which has a degree of identity to the amino acid sequence set forth in SEQ ID NO:27, SEQ ID NO:29, or SEQ ID NO:33 of at least about 65%, preferably about 70%, preferably about 75%, preferably about 80%, preferably about 85%, more preferably about 90%, even more preferably about 95%, and most preferably about 97%, which qualitatively retain the activity of the polypeptides (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth SEQ ID NO:27, SEQ ID NO:29, or SEQ ID NO:33. The degree of identity between two or more amino acid sequences may be determined by means of computer programs known in the art such as GAP provided in the GCG program package (Needleman and Wunsch, 1970, *Journal of Molecular Biology* 48:443–453). For purposes of determining the degree of identity between two amino acid sequences for the present invention, the Clustal method (DNASTAR, Inc., Madison, Wis.) is used with an identity table, a gap penalty of 10, and a gap length of 10.

The amino acid sequences of the homologous polypeptides differ from the amino acid sequence set forth in SEQ ID NO:27, SEQ ID NO:29, or SEQ ID NO:33 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine) and small amino acids (such as glycine, alanine, serine, threonine and methionine). Amino acid substitutions which do not generally alter the specific activity are known in the art and are described, e.g., by H. Neurath and R. L. Hill, 1979, In, *The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The present invention also relates to polypeptides having immunochemical identity or partial immunochemical identity to the polypeptides having laccase activity which are native to *Coprinus cinereus* IFO 8371. A polypeptide having immunochemical identity to the polypeptide native to *Coprinus cinereus* IFO 8371 means that an antiserum containing antibodies against the antigens of the native polypeptide reacts with the antigens of the other polypeptide in an identical fashion such as total fusion of precipitates, identical precipitate morphology, and/or identical electrophoretic mobility using a specific immunochemical technique. A further explanation of immunochemical identity is described by Axelsen, Bock, and Kroll, In N. H. Axelsen, J. Krøll, and B. Weeks, editors, *A Manual of Quantitative Immunoelectrophoresis*, Blackwell Scientific Publications, 1973, Chapter 10. Partial immunochemical identity means that an antiserum containing antibodies against the antigens of the native polypeptide reacts with the antigens of the other polypeptide in an partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11. The immunochemical properties are determined by immunological cross-reaction identity tests by the well-known Ouchterlony double immunodiffusion procedure. Specifically, an antiserum against the polypeptide of the invention is raised by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). Monoclonal antibodies may be prepared, e.g., according to the methods of E. Harlow and D. Lane, editors, 1988, *Antibodies, A Laboratory Manual*, Cold Spring Harbor Press, Cold Spring Harbor, N.Y. Purified immunoglobulins may be obtained from the antiserum, e.g., by ammonium sulfate precipitation, followed by dialysis and ion exchange chromatography (e.g., DEAE-Sephadex).

Homologous polypeptides and polypeptides having identical or partially identical immunological properties may be obtained from microorganisms of any genus, preferably from a bacterial or fungal source. Sources for homologous genes are strains of the family Coprinaceae, preferably of the genus Coprinus and species thereof available in public depositories. Furthermore, homologous genes may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., supra).

As defined herein, an "isolated" polypeptide is a polypeptide which is essentially free of other non-laccase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Nucleic Acid Sequences

The present invention also relates to isolated nucleic acid sequences obtained from a Coprinus strain, which encode a polypeptide of the present invention. In a preferred embodiment, the nucleic acid sequence encodes a polypeptide obtained from *Coprinus cinereus* and in a more preferred embodiment, the nucleic acid sequence is obtained from *Coprinus cinereus* IFO 8371, e.g., the nucleic acid sequence set forth in SEQ ID NO:26, SEQ ID NO:28, or SEQ ID NO:32. The present invention also encompasses nucleic acid sequences which encode a polypeptide having the amino acid sequence set forth in SEQ ID NO:27, SEQ ID NO:29, or SEQ ID NO:33, which differ from SEQ ID NO:26, SEQ ID NO:28, or SEQ ID NO:32, respectively, by virtue of the degeneracy of the genetic code.

As described above, the nucleic acid sequences may be obtained from microorganisms which are synonyms of Coprinus as defined by Webster, 1980, supra.

The techniques used to isolate or clone a nucleic acid sequence encoding a polypeptide are known in the art and include isolation from genomic DNA, preparation from cDNA, or a combination thereof. The cloning of the nucleic sequences of the present invention from such genomic DNA can be effected, e.g., by using the well known polymerase chain reaction (PCR). See, e.g., Innis et al., 1990, *A Guide to Methods and Application*, Academic Press, New York. The nucleic acid sequence may be cloned from a strain of the Coprinus producing the polypeptide, or another or related organism and thus, for example, may be an allelic or species variant of the polypeptide encoding region of the nucleic acid sequence.

The term "isolated nucleic acid sequence" as used herein refers to a nucleic acid sequence encoding a polypeptide of the present invention which is isolated by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a nucleic acid sequence which has a degree of identity to the nucleic acid sequence set forth in SEQ ID NO:26, SEQ ID NO:28, SEQ ID NO:32, or subsequences thereof of at least about 65%, preferably about 70%, preferably about 75%, preferably about 80%, preferably about 85%, more preferably about 90%, even more preferably about 95%, and most preferably about 97%, which encode an active polypeptide. The degree of identity between two nucleic acid sequences may be determined by means of computer programs known in the art such as GAP provided in the GCG program package (Needleman and Wunsch, 1970, *Journal of Molecular Biology* 48:443–453). For purposes of determining the degree of identity between two nucleic acid sequences for the present invention, the Clustal method (DNASTAR, Inc., Madison, Wis.) is used with an identity table, a gap penalty of 10, and a gap length of 10.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:26, SEQ ID NO:28, or SEQ ID NO:32, e.g., a sub-sequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2:95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244:1081–1085). In the latter technique mutations are introduced at every residue in the molecule, and the resultant mutant molecules are tested for laccase activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (see, e.g., de Vos et al., 1992, *Science* 255, 306–312; Smith et al., 1992, *Journal of Molecular Biology* 224:899–904; Wlodaver et al., 1992, *FEBS Letters* 309, 59–64).

Polypeptides of the present invention also include fused polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The present invention also relates to nucleic acid sequences which are capable of hybridizing under standard conditions with an oligonucleotide probe which hybridizes under the same conditions with the nucleic acid sequence set forth in SEQ ID NO:26, SEQ ID NO:28, SEQ ID NO:32, a subsequence thereof, or its complementary strand (Sambrook et al., supra). Hybridization indicates that the analogous nucleic acid sequence hybridizes to the oligonucleotide probe corresponding to the polypeptide encoding part of the nucleic acid sequence shown in SEQ ID NO:26, SEQ ID NO:28, or SEQ ID NO:32 under standard conditions.

The amino acid sequence set forth in SEQ ID NO:27, SEQ ID NO:29, or SEQ ID NO:33 or a partial amino acid sequence thereof may be used to design an oligonucleotide probe, or a gene encoding a polypeptide of the present invention or a subsequence thereof can also be used as a probe, to isolate homologous genes of any genus or species. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes, preferably no more than 1200 nucleotides in length, can also be used. Both DNA and RNA probes can be used. The probes are typically labeled for detecting the corresponding gene (for example, with $^{32}$P, $^1$H, biotin, or avidin). A PCR reaction using the degenerate probes mentioned herein and genomic DNA or first-strand cDNA from a *Coprinus cinereus* can also yield a *Coprinus cinereus* laccase-specific product which can then be used as a probe to clone the corresponding genomic or cDNA.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac gene (DeBoer et al., 1983, *Proceedings of the National Academy of Sciences USA* 80:21–25). Further promoters are described in "Useful proteins from recombinant bacteria" in S*cientific American*, 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof.

Particularly preferred promoters for use in filamentous fungal host cells are the TAKA amylase, NA2-tpi (a hybrid of the promoters from the genes encoding *Aspergillus niger* neutral α-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the Saccharomyces cerevisiae alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15:5983–5990. Polyadenylation sequences are well known in the art for mammalian host cells.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the laccase relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the α-factor from *Saccharomyces cerevisiae*, an amylase or a protease gene from a Bacillus species, or the calf preprochymosin gene. However, any signal peptide coding region capable of directing the expressed laccase into the secretory pathway of a host cell of choice may be used in the present invention.

An effective signal peptide coding region for bacterial host cells is the signal peptide coding region obtained from the maltogenic amylase gene from Bacillus NCEB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9:1355–1364; Jarai and Buxton, 1994, *Current Genetics* 26:2238–244; Verdier, 1990, *Yeast* 6:271–297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further (examples, see Verdier, 1990, supra and MacKenzie et al., 1993, *Journal of General Microbiology* 139:2295–2307.

A chaperone is a protein which assists another polypeptide in folding properly (Hartl et al., 1994, *TIBS* 19:20–25; Bergeron et al., 1994. *TIBS* 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7:1515–11157; Robinson et al., 1994, *Bio/Technology* 1:381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10:67–79; Fuller et al., 1989, *Proceedings of the National Academy of Sciences USA* 86:1434–1438; Julius et al., 1984, *Cell* 37:1075–1089; Julius et al., 1983, *Cell* 32:839–852). The nucleic acid sequence encoding a processing protease may be obtained from the genes encoding *Saccharomyces cerevisiae* dipeptidylarninopeptidase, *Saccharomyces cerevisiae* Kex2, and *Yarrowia lipolytica* dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB10, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism or a non-unicellular microorganism. Useful unicellular cells are bacterial cells such as gram positive bacteria including, but not limited to, a Bacillus cell, e.g., *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus*, a *Bacillus licheniformis*, a *Bacillus subtilis*, or a *Bacillus stearothermophilus* cell. The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnar and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5771–5278).

The host cell may be a eukaryote, such as a mammalian cell, an insect cell, a plant cell or, preferably, a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection. The fungal host cell may be a yeast cell or a filamentous fungal cell.

"Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathern et al., editors, 1981).

"Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

"Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a preferred embodiment, the fungal host cell is a yeast cell. In a more preferred embodiment, the yeast host cell is a cell of a species of Candida, Kluyveromyces, Saccharomyces, Schizosaccharomyces, Pichia, or Yarrowia. In a most preferred embodiment, the yeast host cell is a *Saccharomyces cerevisiae*, a *Saccharomyces carlsbergensis*, a *Saccharomyces diastaticus*, a *Saccharomyces douglasii*, a *Saccharomyces kluyveri*, a *Saccharomyces norbensis*, or a *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. In a more preferred embodiment, the filamentous fungal host cell is a cell of a species of, but not limited to, Acremonium, Aspergillus, Fusarium, Humicola, Myceliophthora, Mucor, Neurospora, Penicillium, Thielavia, Tolypocladium, and Trichoderma. In an even more preferred embodiment, the filamentous fungal host cell is an Aspergillus cell. In another even more preferred embodiment, the filametitous fungal host cell is a Fusariun cell. In a most preferred embodiment, the filamentous fungal host cell is an *Aspergillus oryzae*, an *Aspergillus niger*, an *Aspergillus foetidus*, Lan or an *Aspergillus japonicus* cell. In another most preferred embodiment, the filamentous fungal host cell is a *Fusarium oxysporum* or a *Fusarium graminearum* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Methods of Production

The present invention also relates to methods for producing a polypeptide of the present invention comprising (a) cultivating a Coprinus strain to produce a supernatant comprising the polypeptide; and (b) recovering the polypeptide.

The present invention also relates to methods for producing a polypeptide of the present invention comprising (a) cultivating a host cell under conditions conducive to expression of the polypeptide; and (b) recovering the polypeptide.

In both methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, Calif., 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining laccase activity are known in the art and include, e.g., the oxidation of 2,2'-azinobis-(3-ethybenzthiazoline-6-sulfonic acid (ABTS) (Childs et al., 1975, *Biochemical Journal* 145:93–103) or syringaldazine (Bauer et al., 1971, *Analytical Chemistry* 43: 421–425) as substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J. -C. Janson and Lars Ryden, editors, VCH Publishers, New York, 1989).

Uses

The polypeptides of the present invention may be used in a number of different industrial processes. These processes include polymerization of lignin, both Kraft and lignosulfates, in solution, in order to produce a lignin with a higher molecular weight. A neutral/alkaline laccase is a particular advantage in that Kraft lignin is more soluble at higher pHs. Such methods are described in, for example, Jin et al., 1991, *Holzforschung* 45: 467–468; U.S. Pat. No. 4,432,921; EP 0 275 544; PCT/DK93/00217, 1993. Laccase is also useful in the copolymerization of lignin with low molecular weight compounds, such as is described by Milstein et al., 1994, *Appl. Microbiol. Biotechnol.* 40: 760–767.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, *Current Opinion in Biotechnology* 3: 261–266, 1992; *Journal of Biotechnology* 25: 333–339, 1992; Hiroi et al., 1976, *Svensk Papperstidning* 5:162–166, 1976. Since the environment in a paper mill is typically alkaline, the present laccase is more useful for this purpose than other known laccases, which function best under acidic conditions.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; WO 92/18687; WO 91/05839; EP 0495836; Calvo, 1991, *Mededelingen van de Faculteit Landbouw-wetenschappen/Rijiksuniversitet Gent.* 56: 1565–1567; Tsujino et al., 1991, *J. Soc. Chem.* 42: 273–282. Laccases of the present invention are particularly useful in oxidation at high pH, i.e., over pH 7, as disclosed in DK 0982/94, the contents of which are incorporated herein by reference. Use of laccase in oxidation of dye precursors for hair dyeing is disclosed in U.S. Pat. No. 3,251,742, the contents of which are incorporated herein by reference.

The present laccase can also be used for the polymerization or oxidation of phenolic compounds present in liquids. An example of such utility is the treatment of juices, such as apple juice, so that the laccase will accelerate a precipitation of the phenolic compounds present in the juice, thereby producing a more stable juice. Such applications have been described by Stutz, Fruit processing 7/93, 248–252, 1993; Maier et al., 1990, *Dt. Lebensmittel-rindschau* 86: 137–142; Dietrich et al., 1990, *Fluss. Obst.* 57: 67–73.

Laccases of the present invention are also useful in soil detoxification (Nannipieri et al., 1991, *J. Environ. Qual.* 20: 510–517; Dec and Bollag, 1990, *Arch. Environ. Contam. Toxicol.* 19: 543–550).

The present invention is further described by the following examples which should not be construed as limiting the scope of the invention.

EXAMPLES

Materials and strains

Chemicals used as buffers and substrates are commercial products of at least reagent grade. Strains used are *Coprinus cinereus* A3387 (IFO 8371), *E. coli* Y1090(ZL) (GIBCO BRL, Gaithersburg, Md.), *E. coli* DH10B(ZL) (GIBCO BRL), *E. coli* DH5α (Stratagene, La Jolla, Calif.), *Aspergillus oryzae* HowB712, *Aspergillus oryzae* JeRS317, and *Aspergillus oryzae* JeRS316.

Example 1

Purification and characterization of *Coprinus cinereus* laccase

The laccase is initially isolated from *Coprinus cinereus* strain A3387 culture broth by filtration (Propex 23+HSC) and concentration (Filtron 2×10K). The cationic flocculent Magnifloc® 521C (American Cyanamid, Wallingford, Conn.) is added to the resulting preparation, mixed for 30 minutes, and then centrifuged. This step removes colored substances from the preparation. The supernate is then precipitated with ammonium sulfate (55% saturation) and resuspended twice in ammonium sulfate (40% saturation), which also results in color removal. The resuspension is further concentrated to reduce the volume, and filtered, but not washed out. The concentrate in ammonium sulfate (40% saturation) is then subjected to Butyl ToyoPearl hydrophobic chromatography (Tosoh Corp., Tokyo, Japan) and eluted with an ammonium sulfate gradient from 40% to 0% saturation. Buffer exchange to 20 mM MES pH 6.0 and concentration with an Amicon cell equipped with a membrane of 20,000 molecular weight cut-off is then conducted. The resulting soluti.on is then subjected to Q-Sepharose (Pharmacia, Uppsala, Sweden) anion exchange chromatography (150 ml) in 20 mM MES pH 6.0 with a linear gradient from 0 to 0.4 M NaCl. The sample is finally rechromatographed by HPQ-Sepharose (Pharmacia, Upsala, Sweden) chromatography (50 ml) in 20 mM MES pH 6.0 with a linear gradient from 0 to 0.4 M NaCl. The laccase elutes at 0.25–0.30 M NaCl.

The purified laccase is about 95% pure as determined by SDS-PAGE which shows the laccase as a band of $M_W$=63,000. Isoelectric focusing shows two dominating bands with pIs of 3.7 and 4.0.

The N-terminal amino acid residue of the purified laccase is blocked. The laccase is therefore reduced, S-carboxymethylated, and digested with Endoproteinase Lys-C (Boehringer Mannheim, Indianapolis, Ind.) and with chymotrypsin. The resulting peptides are purified by reversed phase HPLC using a Vydac C18 column (Vydac, Inc., Hesperia, Calif.) eluted with a linear gradient of either acetonitrile or 2-propanol in 0.1% aqueous trifluoroacetic acid. The purified peptides are sequenced on an Applied Biosystems 473A Protein Sequencer according to the manufacture's instructions.

Several distinct peptides which result from the protease digestion are listed below. In the following sequences, Xaa represents an indeterminable residue. Peptide 3 apparently encompasses peptide 2. In peptides 4 and 9, residues designated Xaa/Yaa indicate both residues are found at that position. Residues in parentheses are uncertain. Peptide 9 is included in peptide 13.

Peptide 1 (SEQ ID NO: 1):
Glu-Val-Asp-Gly-Gln-Leu-Thr-Glu-Pro-His-Thr-Val-Asp-Arg-Leu-Gln-Ile-Phe-Thr-Gly-Gln-Arg-Tyr-Ser-Phe-Val-Leu-Asp-Ala-Asn-Gln-Pro-Val-Asp-Asn-Tyr-Trp-Ile-Arg-Ala
Peptide 2 (SEQ ID NO: 2):
Xaa-Xaa-Asp-Asn-Pro-Gly-Pro
Peptide 3 (SEQ ID NO: 3):
Phe-Val-Thr-Asp-Asn-Pro-Gly-Pro
Peptides 2 and 3 combined (SEQ ID NO: 4):
Phe-Val-Thr-Asp-Asn-Pro-Gly-Pro-Trp
Peptide 4 (SEQ ID NO: 5):
Ile/Leu-Asp-Pro-Ala-Xaa-Pro-Gly-Ile-Pro-Thr-Pro-Gly-Ala-(Ala)-Asp-Val
Peptide 5 (SEQ ID NO: 6):
Gly-Val-Leu-Gly-Asn-Pro-Gly-Ile
Peptide 6 (SEQ ID NO: 7):
Xaa-Phe-Asp-Asn-Leu-Thr-Asn
Peptide 7 (SEQ ID NO: 8):
Tyr-Arg-Xaa-Arg-Leu-Ile-Ser-Leu-Ser-Cys-Asn-Pro-Asp-(Trp)-Gln-Phe
Peptide 8 (SEQ ID NO: 9):
Ala-Asp-Trp-Tyr
Peptide 9 (SEQ ID NO: 10):
Ile-Pro-Ala/Asp-Pro-Ser-Ile-Gln
Peptide 10 (SEQ ID NO: 11):
Glue-Ser-Pro-Ser-Val-Pro-Thr-Leu-Ile-Arg-Phe
Peptide 11 (SEQ ID NO: 12):
Ala-Gly-Thr-Phe
Peptide 12 (SEQ ID NO: 13):
Ser-Gly-Ala-Gln-Ser-Ala-Asn-Asp-Leu-Leu-Pro-Ala-Gly
Peptide 13 (SEQ ID NO: 14):
Ile-Pro-Ala-Pro-Ser-Ile-Gln-Gly-Ala-Ala-Gln-Pro-Asx-Ala-Thr Most of the peptides show considerable homology with portions of the amino acid sequence of a *Polyporus pinsitus* laccase (Yaver et al., 1995, *Applied and Environmental Microbiology* 62: 834–841).

Example 2
RNA isolation

*Coprinus cinereus* strain A3387 is cultivated at 26° C. in FG4 medium comprised of 30 g of soybean meal, 15 g of maltodextrin, 5 g of Bacto peptone, and 0.2 g of pluronic acid per liter. The mycelia are harvested after six days of growth, frozen in liquid $N_2$, and stored at −80° C. Total RNA is prepared from the frozen, powdered mycelium of *Coprinus cinereus* A3387 by extraction with guanidinium thiocyanate followed by ultracentrifugation through a 5.7 M cesium chloride cushion (Chirgwin et al., 1979, *Biochemistry* 18: 5294–5299). Poly(A)+ RNA is isolated by oligo (dT)-cellulose affinity chromatography according to Aviv and Leder (1972, *Proceedings of the National Academy of Sciences USA* 69: 1408–1412).

Example 3
Construction of a cDNA library

Double-stranded cDNA is synthesized from 5 µg of *Coprinus cinereus* poly(A)+ RNA of Example 2 as described by Gubler and Hoffman (1983, *Gene* 25: 263–269) and Sambrook et al. (1989, *Molecular Cloning: A Laboratory Manual*, Cold Spring Harbor Press, Cold Spring Harbor, N.Y.), except that an oligo(dT)-NotI anchor primer, instead of an oligo(dT)12–18 primer, is used in the first strand reaction. After synthesis, the cDNA is treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA is digested with NotI, size-fractionated for 1.2–3.0 kb cDNAs by agarose gel electrophoresis, and ligated into BstXI/NotI cleaved pYES2.0 vector (Invitrogen, San Diego, Calif.). The ligation mixture is transformed into electrocompetent *E. coli* DH10B cells (Life Technologies, Gaithersburg, Md.) according to the manufacturer's instructions. The library consisting of 1×10⁶ independent clones is stored as individual pools (25,000–30,000 colony forming units/pool) in 20% glycerol at −80° C., and as double stranded cDNA and ligation mixture at −20° C.

Example 4
Generation of a cDNA probe from a *Coprinus cinereus* cDNA using PCR

Three oligonucleotides (sense s1 and s2 and antisense as1) with low codon degeneracy are designed based on two conserved motifs in laccases from Rhizoctonia, Phlebia, Polyporus, and Coriolus. The oligos have the following sequences:

s1: 5'-ATI CAc/t TGG CAc/t GGI c/tTI c/tTI-3' (SEQ ID NO:15)

s2: 5'-ATI CAc/t TGG CAc/t GGI TTc/t Ttc/t-3' (SEQ ID NO:16)

as1: 3'-GGI ACC AAa/g a/gAI GTa/g ACa/g GTa/g TAI CT-5' (SEQ ID NO:17)

One µg of plasmid DNA from the *Coprinus cinereus* library pool described in Example 3 is PCR amplified in a thermal cycler according to Frohman et al., 1988, *Proceedings of the National Academy of Sciences USA* 85: 8998–9002 using 500 pmol of each laccase sense primer in two combinations (s1 and as1, s2 and as1) with 500 pmol of the laccase antisense primer, and 2.5 units of Taq polymerase (Perkin Elmer Cetus, Branchburg, N.J.). Thirty cycles of PCR are performed using a cycle profile of denaturation at 94° C. for 1 minute, annealing at 55° C. for two minutes, and extension at 72° C. for 3 minutes. Analysis of the PCR products reveals a 1.2 kb major PCR product with one primer pair, s1 and as1, whereas the other pair does not amplify any major products. The PCR fragment of interest is subcloned into a pUC18 vector and sequenced according to Siggaard-Andersen et al., 1991, *Proceedings of the National Academy of Sciences USA* 88: 4114–4118. Sequencing of the ends of two PCR subclones in pUC18 reveals a cDNA sequence coding for a laccase polypeptide. In addition to the primer encoding residues, the deduced amino acid sequence aligns with two peptide sequences obtained from the purified wild-type laccase, indicating that PCR has specifically amplified the desired region of a *Coprinus cinereus* laccase cDNA.

Example 5
Subcloning and sequencing of partial cDNAs

The PCR product described in Example 4 is ligated into pCRII using a TA Cloning Kit (Invitrogen, San Diego, Calif.) according to the manufacturer's instructions. Seven subclones are prepared and sequenced using both the M13 universal −21mer oligonucleotide and the M13 −48 reverse oligonucleotide. Nucleotide sequences are determined on both strands by primer walking using Taq polymerase cycle-sequencing with fluorescent-labeled nucleotides, and reactions are electrophoresed on an Applied Biosystems Automatic DNA Sequencer (Model 373A, version 2.0.1).

The seven clones based on deduced amino acid sequence and percent identities between them appear to encode for 3 laccases (Table 1). Clones CCLACC4, 8 and 7 are designated as partial cDNAs of *Coprinus cinereus* lcc1 (SEQ ID NOS:18 and 19). Clones CCLACC 1, 3 and 11 (pDSY71) are designated as partial cDNAs of *Coprinus cinereus* lcc2 (SEQ ID NOS:20 and 21). Clone CCLACC 15 (pDSY72) is designated as a partial cDNA of *Coprinus cinereus* lcc3 (SEQ ID NOS:22 and 23). The deduced amino acid sequences of the partial cDNAs of lcc1, lcc2, and lcc3 (SEQ ID NOS:19, 21, and 23) are compared to the peptide sequences determined above, and the closest match is found between lcc1 and the peptide sequences. In order to obtain a full-length clone for heterologous expression of lcc1 in *Aspergillus oryzae*, a genomic library of *Coprinus cinereus* A3387 is constructed in λZipLox.

TABLE 1

Percent identities between *Coprinus cinereus* cDNAs

|   |          | 1  | 2   | 3  | 4  | 5  | 6  | 7  |
|---|----------|----|-----|----|----|----|----|----|
| 1 | CCLACC4  |    | 98  | 100| 65 | 65 | 65 | 62 |
| 2 | CCLACC7  |    |     | 98 | 65 | 64 | 65 | 63 |
| 3 | CCLACC8  |    |     |    | 65 | 65 | 65 | 62 |
| 4 | CCLACC1  |    |     |    |    | 100| 99 | 81 |
| 5 | CCLACC3  |    |     |    |    |    | 99 | 81 |
| 6 | CCLACC11 |    |     |    |    |    |    | 81 |
| 7 | CCLACC15 |    |     |    |    |    |    |    |

Example 6
Genomic DNA isolation

A culture of *Coprinus cinereus* A3387 is grown at room temperature for 4 days with shaking at 200 rpm in YEG medium comprised of 0.5% yeast extract and 2% dextrose. Mycelia are harvested through Miracloth (Calbiochem, La Jolla, Calif.), washed twice with 10 mM Tris-0.1 mM EDTA pH 7.4 buffer (TE) and frozen quickly in liquid nitrogen. DNA is isolated as described by Timberlake and Barnard, 1981, *Cell* 26: 29–37.

Example 7
Preparation of *Coprinus cinereus* genomic library

A genomic library of *Coprinus cinereus* A3387 is constructed using a λZipLox Kit (Life Technologies, Gaithersburg, Md.) according to the manufacturer's instructions. Genomic DNA (~30 μg) is digested with Tsp509I (New England Biolabs, Beverly, Mass.) at 65° C. in a total volume of 150 μl in the buffer provided by the supplier. Samples of 30 μl are taken at 3, 5, 7, 8, and 9 minutes and electrophoresed on a 1% agarose preparative gel. Bands of 3 to 8 kb in size are excised from the gel. The DNA is then isolated from the gel slices using a Qiaex Kit (Qiagen, San Diego, Calif.). The size-fractionated DNA is ligated overnight at room temperature to λZipLox EcoRI arms following the protocols provided with the kit. The ligations are packaged into phage using a Giga Pak Gold Packaging Kit (Stratagene, La Jolla, Calif.), and the packaging reactions are titered using *E. coli* Y1090 cells. A total of 6×10$^5$ pfu are obtained. The packaging extract is plated to amplify the library, and the titer of the library is determined to be 1×10$^{11}$ pfu/ml. Twenty individual plaques are picked, and the plasmids are excised from the plaques by passage through *E. coli* DH10B. Plasmid DNA is isolated from the cultures and is digested with PstI/NotI to determine the percent of molecules in the library which have inserts. Eight of the twenty, or 40% of those tested, have inserts which range in size from 3 to 6 kb.

Example 8
Probe preparation for library screening

A DIG-labeled probe for nonradioactive screening of the library is prepared by PCR using the *Coprinus cinereus* partial lcc1 cDNA described in Example 5 as a template. The primers used in the reaction are shown below:

5' ACTGCGATGGTCTCCGTGGTC 3' (SEQ ID NO:24)
5' GGGGCCTGGGTTATCGGTGAC 3' (SEQ ID NO:25)

The PCR conditions are 1 cycle at 95° C. for 5 minutes, 50° C. for 1 minute, and 72° C. for 1.5 minutes; 29 cycles each at 95° C. for 1 minute, 50° C. for 1 minute, and 72° C. for 1.5 minutes; and 1 cycle at 95° C. for 30 seconds, 50° C. for 1 minute, and 72° C. for 3 minutes. The reaction contains 0.1 μg of the *Coprinus cinereus* partial lcc1 cDNA, 10 μl 10× PCR Buffer (Perkin Elmer, Branchburg, N.J.), 5 μl 10× DIG labeling mix (Boehringer Mannheim, Indianapolis, Ind.), 75 pmol of each primer, and 0.5 unit of Taq DNA polymerase (Perkin-Elmer Corp., Branchburg, N.J.). A probe concentration of 250 ng/μl is determined after PCR following protocols provided with the Genius Kit (Boehringer Mannheim, Indianapolis, Ind.).

$^{32}$P-labeled probes of *Coprinus cinereus* lcc2 and lcc3 partial cDNAs are prepared using a RadPrime Kit (Life Technologies, Gaithersburg, Md.) according to the manufacturer's instructions.

Example 9
Genomic library screening

Appropriate dilutions of the λZipLox *Coprinus cinereus* genomic library are plated with *E. coli* Y1090 cells on NZY plates comprised of 0.5% NaCl, 0.2% MgSO$_4$, 0.5% yeast extract, and 1% NZ amine pH 7.5 per liter with 0.7% top agarose. The plaques are lifted to Hybond N+ filters (Amersham Co., Amersham, UK) using standard procedures (Sambrook et al. 1989, supra). The filters are hybridized in Engler Blue hybridization buffer at 65° C. for 1 hour. After prehybridization, the DIG labeled probe of Example 8 is added at a final concentration of 3 ng/ml and allowed to hybridize overnight at 65° C. The filters are washed at 65° C. twice for 5 minutes in 2× SSC, 0.1% SDS, twice for 15 minutes in 0.5× SSC, 0.1%SDS, and then are processed to detect the hybridized DIG-label using the Genius Kit and Lumi-Phos 530 substrate according to the manufacturer's instructions. Following the detection protocol, film is placed on top of the filters for 2 hours.

For screening of the library using the $^{32}$P-labeled probes described in Example 8, filter lifts are prepared as described above, and prehybridized at 65° C. in 2× SSPE, 1% SDS, 0.5% nonfat dry milk and 200 μg denatured salmon sperm DNA. After 1 hour prehybridization, the $^{32}$P-labeled probes are added to a final concentration of $10^6$ cpm/ml and hybridizations are continued overnight at 65° C. The filters are washed twice at 65° C. for 15 minutes in 0.2× SSC, 1% SDS, and 0.1% sodium pyrophosphate.

The genomic library is probed with the DIG-labeled fragment of lcc1. Approximately 200,000 plaques are screened using the conditions described above, and 9 positive clones are obtained. The plasmids are excised from the clones by passage through E. coli DH10B(ZL), and then are characterized by digestion with PstI/NotI. All 9 clones contain inserts. Based on the nucleotide sequence of the partial lcc1 cDNA, the genomic clones which may be lcc1 genomic clones are determined. All 8 unique clones are digested with BamHI/PstI and PstI/BsmI for which fragments of 205 bp and 382 bp, respectively, are expected (neither lcc2 nor lcc3 partial cDNAs contain these fragments). Four of the 8 unique clones contain both predicted fragments. DNA sequencing reactions on all four clones using universal sequencing primers are performed as described in Example 5 to determine which clones are full-length.

The nucleotide sequence of clone 4–19 (pDSY73) is determined completely on both strands and shown to contain the full length lcc1 gene (FIG. 1, SEQ ID NO:26). The deduced amino acid sequence (FIG. 1, SEQ ID NO:27) of the genomic lcc1 matches 100% with the determined N-terminal sequence (see Example 14) although the predicted signal peptide cleavage site is between A18 and Q19 while the peptide sequence begins 4 residues downstream at S23. The lcc1 gene contains 7 introns ranging in size from 54 to 77 bp. The deduced protein contains 3 potential N-glycosylation sites (AsnXaaThr/Ser), and the predicted mature protein after removal of the signal peptide is 521 amino acids in length. The percent identities of the lcc1 protein to other fungal laccases is shown in Table 2. The highest percent identity, 57.8%, is found when compared to the laccase from the unidentified basidiomycete PM1 (Coll et al., 1993, supra). When alignments of Lcc1 and other basidiomycete laccases are performed, it appears that Lcc1 may have either a C-terminal extension or a C-terminal peptide that is removed by processing.

The genomic library is also screened with the $^{32}$P-labeled probes for the Coprinus cinereus lcc2 and lcc3 partial cDNAs. For screening with the lcc2 probe, approximately 50,000 plaques are hybridized with the probe, and 4 positive clones are obtained. For screening of the library with the lcc3 probe, approximately 35,000 plaques are probed, and 2 positive clones are obtained. After passage through E. coli and isolation of the plasmid DNA, the nucleotide sequence of one of the lcc3 clones (pDSY100) is determined by primer walking as described in Example 5 (FIG. 2, SEQ ID NO:28). The lcc3 gene contains 13 introns (as indicated by lowercase in FIG. 2). The positions of introns 4 through 10 are confirmed from the partial cDNA while the positions of the other 6 introns are deduced based on the consensus sequences found at the 5' and 3' splice sites of fungal introns and by homology of the deduced amino acid sequence (FIG. 2, SEQ ID NO:29) to other laccases. The lcc3 gene encodes for a precursor protein of 517 amino acids. There is one potential N-glycosylation site, and the mature protein after the predicted signal peptide cleavage (indicated by an arrow) is 501 amino acids in length.

From the nucleotide sequences of the 4 positive lcc2 clones, it is observed that none of the clones are full-length. The clone with the largest insert (CCLACC1-4) is missing the sequence coding for the last approximately 100 amino acids based on homology to other fungal laccases.

TABLE 2

Percent identities of the Coprinus cinereus lcc1 to other fungal* laccases

| | Cc lcc1 | Cc lcc2 | Cc lcc3 | Tv lcc1 | Tv lcc2 | Tv lcc3 | Tv lcc4 | Tv lcc5 | Ch | Pr | PMI | Ab | Nc |
|---|---|---|---|---|---|---|---|---|---|---|---|---|---|
| Cclcc1 | | | | | | | | | | | | | |
| Cclcc2 | 59.3 | | | | | | | | | | | | |
| Cclcc3 | 57.5 | 79.6 | | | | | | | | | | | |
| Tvlcc1 | 55.5 | 61.3 | 59.5 | | | | | | | | | | |
| Tvlcc2 | 55.7 | 60.9 | 59.5 | 79.6 | | | | | | | | | |
| Tvlcc3 | 57.0 | 61.0 | 58.2 | 62.8 | 84.6 | | | | | | | | |
| Tvlcc4 | 55.5 | 59.2 | 58.8 | 70.3 | 67.1 | 61.4 | | | | | | | |
| Tvlcc5 | 54.4 | 59.3 | 57.9 | 71.1 | 69.1 | 64.6 | 76.5 | | | | | | |
| Ch | 55.5 | 61.5 | 59.3 | 91.4 | 81.4 | 63.0 | 70.1 | 71.3 | | | | | |
| Pr | 50.3 | 59.1 | 57.5 | 63.3 | 61.5 | 62.2 | 63.9 | 63.9 | 6.41 | | | | |
| PMI | 57.8 | 62.8 | 59.4 | 79.6 | 73.7 | 62.2 | 69.1 | 70.1 | 80.2 | 65.7 | | | |
| Ab | 40.3 | 41.7 | 41.9 | 43.7 | 43.1 | 43.6 | 44.6 | 43.1 | 44.1 | 42.5 | 44.4 | | |
| Nc | 25.3 | 25.3 | 24.0 | 25.1 | 23.8 | 24.8 | 21.9 | 24.2 | 25.1 | 23.0 | 24.4 | 25.5 | |

*Cc = Coprinus cinereus; Tv = Trametes villosa; Ch = Coriolus hirsutus; PM1 = unidentified basidiomycete; Pr = Phlebia radiata; Nc = Neurospora crassa; Ab = Agaricus bisporus; 1cc = laccase gene.

Example 10

Probe preparation for library screening to obtain the full length lcc2 gene

A DIG-labeled probe for nonradioactive screening of the library is prepared by PCR using the Coprinus cinereus lcc2 partial genomic clone as template in order to obtain a full-length clone of lcc2. The primers used in the reaction are shown below:

AGCTCGATGACTTTGTTACGG (1868R CCLCC2) (SEQ ID NO:30)

CAGCGCTACTCGTTFCGTTCTC (1460 CCLCC2) (SEQ ID NO:31)

The PCR conditions are 1 cycle at 95° C. for 1 minute; and 30 cycles each at 94° C. for 1 minute, 55° C. for 1 minute, and 72° C. for 2 minutes. The reaction contains 0.1 μg of Coprinus cinereus lcc2 partial genomic clone (CCLACC1-4), 10 μl of 10× PCR Buffer (Perkin Elmer, Branchburg, N.J.), 5 μl of 10× DIG labeling mix (Boehringer Mannheim, Indianapolis, Ind.), 75 pmol of each primer, and 0.5 Unit of Taq DNA polymerase. The concentration of the DIG-labeled probe is determined using the Genius Kit according to the manufacturer's instructions.

Example 11
Genomic library screening to obtain the full length lcc2 gene

Appropriate dilutions of the λZipLox *Coprinus cinereus* genomic library prepared as described in Example 7 are plated with *E. coli* Y1090 cells on NZY plates (0.5% NaCl, 0.2% MgSO$_4$, 0.5% yeast extract, and 1% NZ amine pH 7.5) with 0.7% top agarose. The plaques are lifted to Hybond N+ filters using standard procedures (Sambrook et al., 1989, supra).

Filters are prehybridized in Easy Hyb hybridization buffer (Boehringer Mannheim, Indianapolis, Ind.) at 42° C. for 1 hour, and after prehybridization the DIG labeled probe mentioned above is added at a final concentration of 1 ng/ml. The filters and probe are allowed to hybridize overnight at 42° C. The filters are then washed twice at room temperature for 5 minutes in 2× SSC-0.1% SDS and twice at 68° C. for 15 minutes in 0.1× SSC-0.1% SDS. The filters are next processed to detect the hybridized DIG-label using the Genius Kit and CSPD Ready-To-Use (Boehringer Mannheim, Indianapolis, Ind.) as substrate according to the manufacturer's instructions. Following the detection protocol, film is placed on the filters for 20 minutes to 2 hours.

Figure 3A:
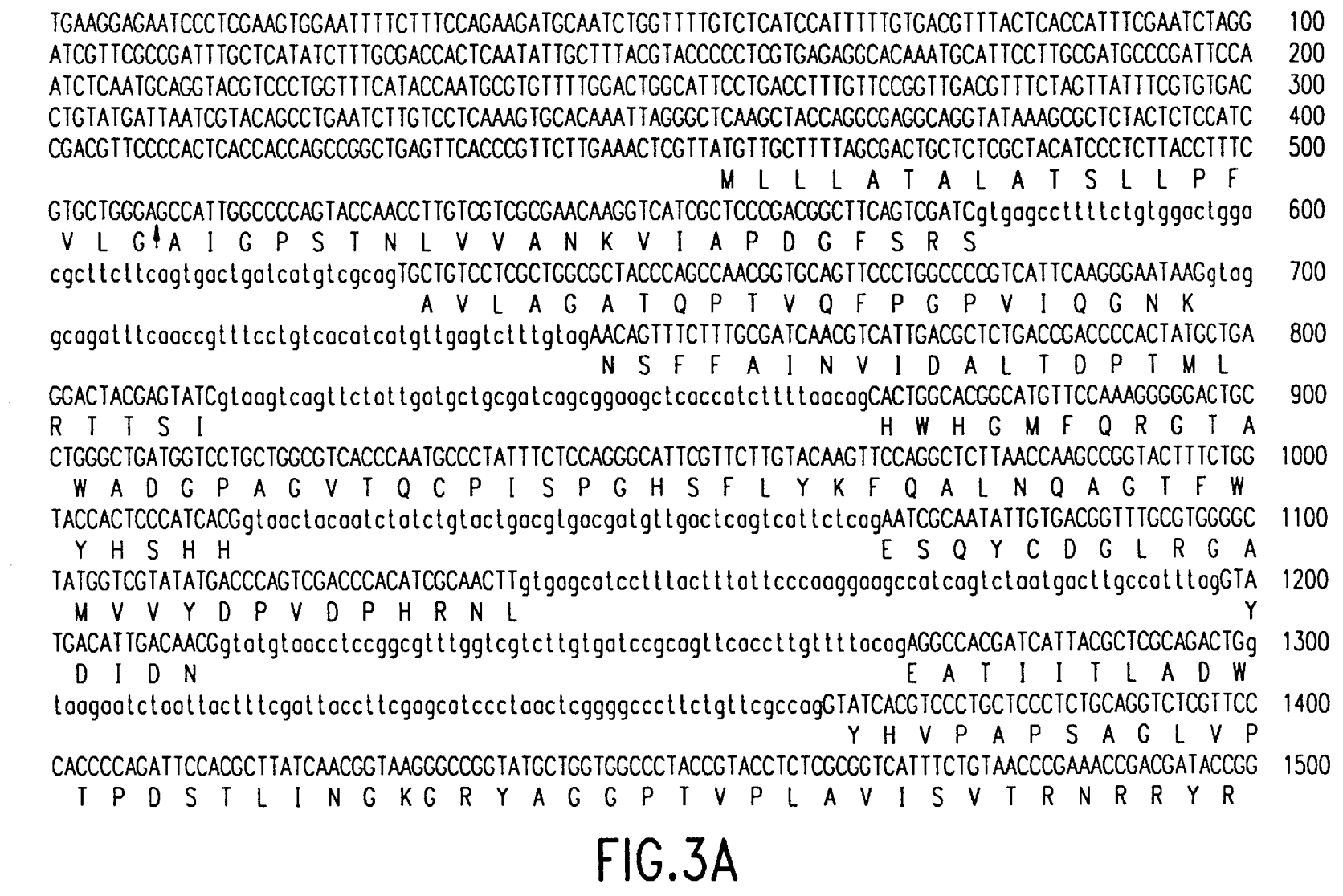

In order to obtain a full-length clone, the genomic library is screened (~42,000 plaques) using a DIG-labeled fragment containing the 3' most 400 bp of the CCLACC1-4 insert. Five positive clones are isolated and purified. Plasmid DNA is excised from all five clones by passage through *E. coli* DH10B. Using a specific primer to the 3' end of the CCLACC1-4 insert in sequencing reactions as described in Example 5, it is determined that only one of the clones (LCC2-5B-1) contains the 3' missing portion of lcc2 gene. However, further sequencing demonstrates that (LCC2-5B-1) does not contain the whole gene but is missing part of the 5' end. Overlapping the sequences of CCLACC1-4 and CCLACC2-5B-1 yields the sequence of the entire gene (FIG. 3, SEQ ID NO:32).

A plasmid pDSY105 containing the full-length lcc2 genomic clone is constructed by ligating together fragments from the LCC2-5B-1 and CCLACC1-4 clones. Clone LCC2-5B-1 is digested with EagI and BglII and electrophoresed on a 1% agarose gel. The gel slice containing the 1.3 kb EagI/BglII fragment is excised, and the DNA is isolated using a Spin Bind column (FMC). A PCR reaction is performed to obtain an EcoRI/BglII fragment containing the N-terminal half of lcc2. The PCR reaction mixture contains 0.1 mg of CCLACC1-4 DNA, 50 pmol each of oligonucleotides 96-0545 and 96-0546, 0.01 mM each of dATP, dCTP, dGTP, and dTTP, and 0.5 U Taq DNA polymerase. PCR conditions are 1 cycle at 95° C. for 5 minutes, 55° C. for 1 minute, and 72° C. for 1 minute; and 30 cycles each at 95° C. for 30 seconds, 55° C. for 1 minute, and 72° C. for 1 minute. The primers used in the reaction are:

96-0545: AGAATTGACTCCACCGACGAA (SEQ ID NO:34)

96-0546: GAATTCTGGCATTCCTGACCTTTGTTC (SEQ ID NO:35)

The desired product of 1.6 kb is subcloned into pCRII using the TA Cloning Kit (Invitrogen, San Diego, Calif.). Partial nucleotide sequences of the subclones are determined using M13-20 universal and M13 -48 reverse universal primers. The fmal plasmid is constructed by digesting pBluescript SK– with EcoRI/EagI and ligating with the EagI/BglII fragment from LCC2-5B-1 and the BglII/EcoRI fragment from the pCRII subclone. The resulting subclones are screened by restriction digests, and the desired product is designated pDSY105.

The lcc2 gene contains 13 introns (indicated by lowercase in FIG. 3). The positions of introns 4 through 10 are confirmed from the partial cDNA while the positions of the other 6 introns are deduced based on the consensus sequences found at the 5' and 3' splice sites of fungal introns and by homology of the deduced amino acid sequence (FIG. 3, SEQ ID NO:33) to other laccases. The lcc2 gene encodes for a precursor protein of 517 amino acids in length. There is one potential N-glycosylation site, and the mature protein after the predicted signal peptide cleavage is 499 amino acids in length.

From the alignment of the Lcc1, Lcc2 and Lcc3 predicted mature proteins, it appears that unlike Lcc1 neither Lcc2 nor Lcc3 contains the 23 amino acid extension present on Lcc1. Lcc1 shares 59.3% and 57.5% identity with Lcc2 and Lcc3, respectively (Table 2). When compared to other fungal laccases, Lcc2 and Lcc3 have the highest identity (79.6%) with one another. The percent identities shared with other fungal laccases range from a high of 62.8% for Lcc2 and the basidiomycete PM1 laccase to a low of 21.9% for Neospora Crassa laccase.

Figure 4B:
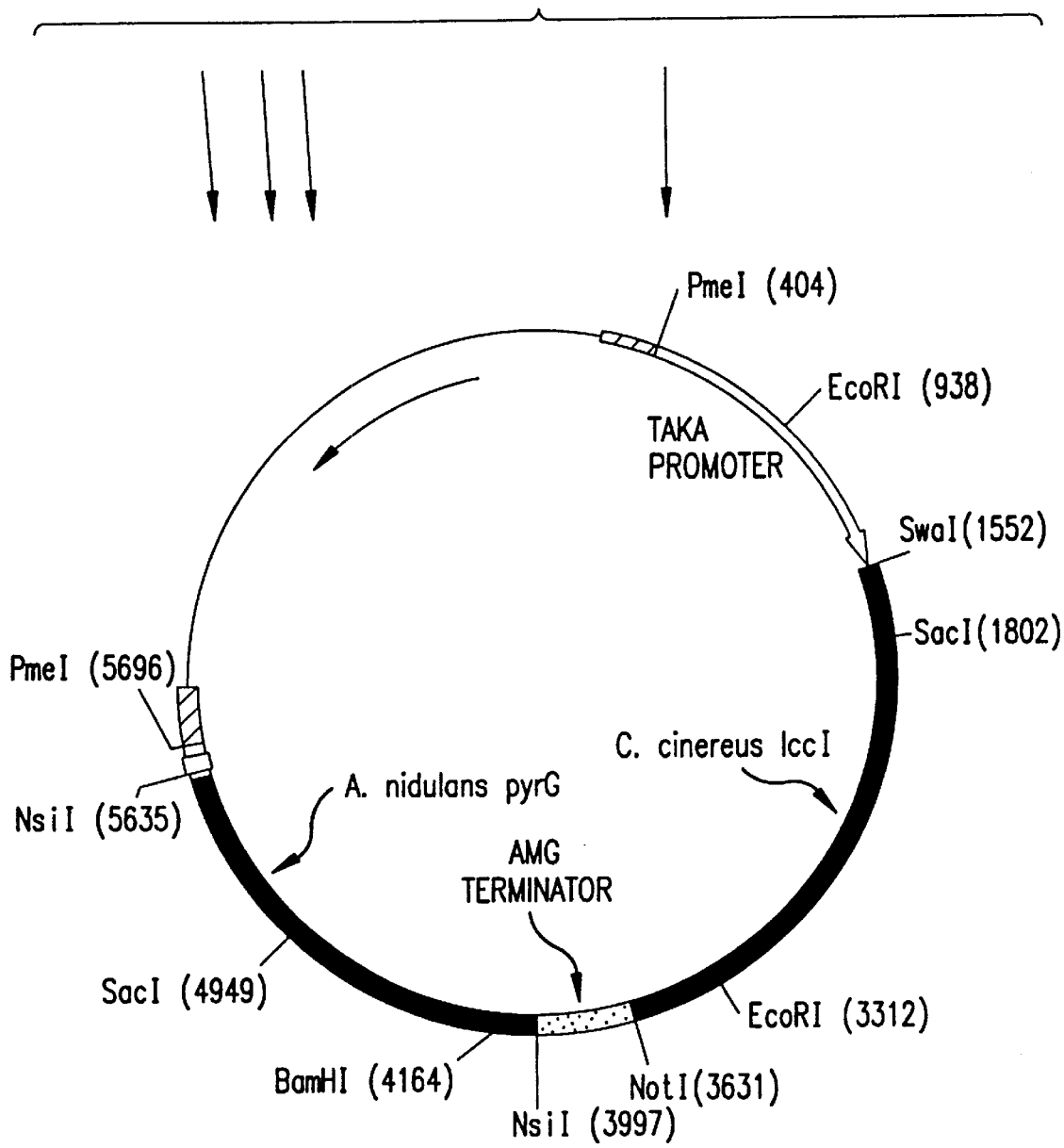
Figure 5:
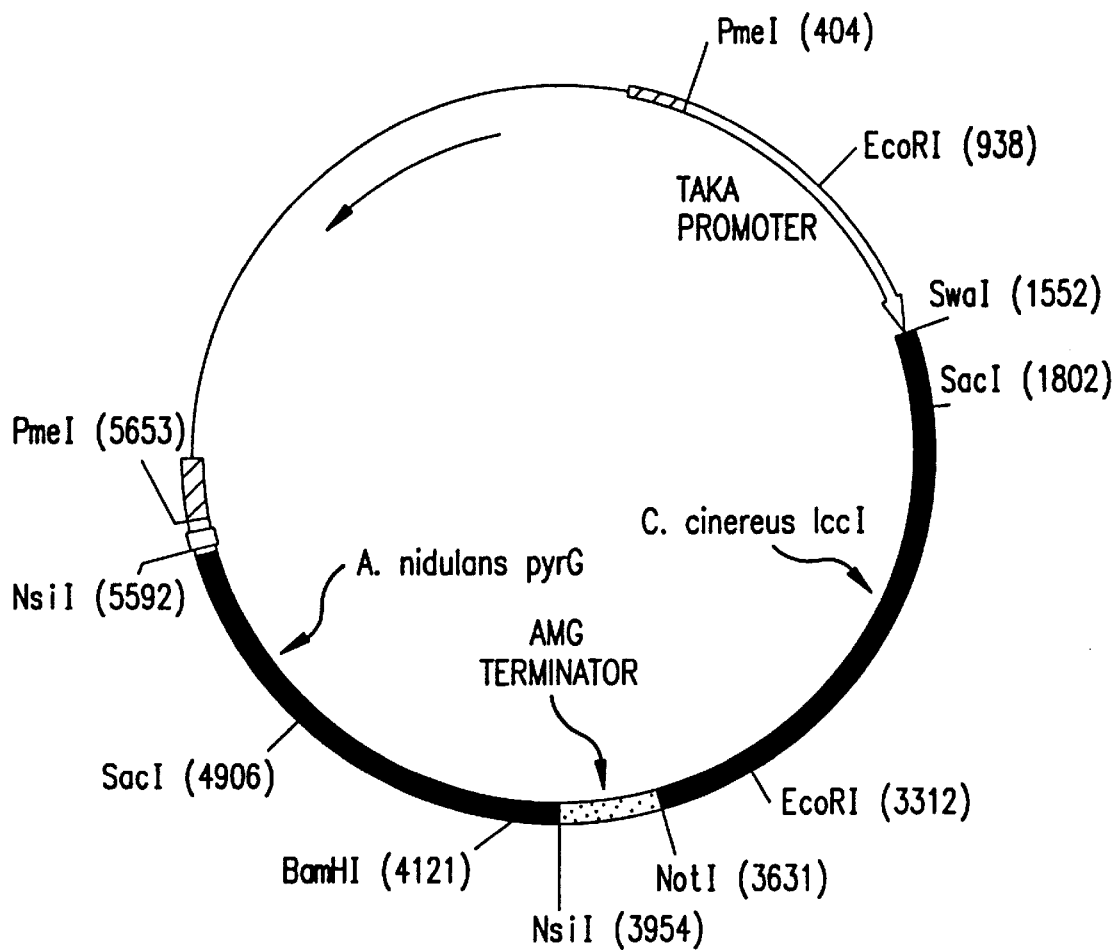
FIG. 5 illustrates a map of plasmid pDSY68.

Example 12
Construction of pDSY67 and pDSY68 for heterologous expression of lcc1 in *Aspergillus oryzae* pDSY67 (FIG. 4) and pDSY68 (FIG. 5) are constructed for expression of *Coprinus cinereus* lcc1 gene. The *Coprinus cinereus* lcc1 gene is cloned into the expression vector pKS4 which contains the TAKA promoter, AMG terminator and the *Aspergillus nidulans* pyrg for selection. The lcc1 gene is inserted as 3 fragments into pKS4 digested with SwaI/NotI to obtain pDSY67 (FIG. 4). Sequencing of pDSY67 reveals the presence of 32 extra base pairs between the stop codon and the AMG terminator. pDSY68 is generated by removing the extra thirty-two base pairs. In order to remove the extra base pairs, pDSY67 is digested with PacI/NotI and the ends are blunted using T4 DNA polymerase. The blunt-end vector is ligated to itself, and the resulting plasmid pDSY68 is sequenced to confirm the extra base pairs are removed.

Example 13
Transformation of *Aspergillus oryzae*

*Aspergillus oryzae* strains HowB712, JeRS316, and JeRS317 are grown for 18 hours in YEG medium at 34° C., and protoplasts are generated and transformed as described by Christensen et al. (1988, *Biotechnology* 6: 1419–1422). The protoplasts are transformed with 10 μg of either pDSY67 or pDSY68. Transformants are selected on Minimal medium plates containing 1.0 M sucrose. Minimal medium plates are comprised of 6.0 g of NaNO$_3$, 0.52 g of KCl, 1.52 g of KH$_2$PO$_4$, 1.0 ml of trace metals solution, 20 g of Nobel Agar (Difco), 20 ml of 50% glucose, 20 ml of methionine (50 g/l), 20 ml of biotin (200 mg/l), 2.5 ml of 20% MgSO$_4$.7H$_2$O, and 1.0 ml of mg/ml streptomycin per liter. The agar medium is adjusted to pH 6.5 prior to autoclaving and then glucose, methionine, biotin, MgSO$_4$.7H$_2$O, and streptomycin are added as sterile solutions to the cooled autoclaved medium and poured into plates. The trace metals solution is comprised of 22 g of ZnSO$_4$.7H$_2$O, 11 g of H$_3$BO$_3$, 5 g of MnCl$_2$.4H$_2$O, 5 g of FeSO$_4$.7H$_2$O, 1.6 g of CoCl$_2$.5H$_2$O, 1.6 g of (NH$_4$)$_6$Mo$_7$O$_{24}$, and 50 g of Na$_4$EDTA per liter.

Example 14
Screening of laccase transformants

Primary transformants are screened first on Minimal medium plates containing 1% glucose as the carbon source and 1 mM 2,2'-azinobis-(3-ethybenzthiazoline-6-sulfonic acid) (ABTS) to test for production of laccase. Transformants producing green zones on the ABTS plates are picked and spore purified before shake flask analysis. For shake flask analysis, the purified transformants are cultivated at 37° C. in MY51 medium comprised of 30 g of maltose, 2 g of $MgSO_4$, 10 g of $KH_2PO_4$, 2 g of $K_2SO_4$, 2 g of citric acid, 10 g of yeast extract, 0.5 ml of trace metals solution, 1 g of urea, 2 g of $(NH_4)_2SO_4$ pH 6.0 per liter. The trace metals solution is comprised of 14.3 g of $ZnSO_4.7H_2O$, 2.5 g of $CuSO_4.5H_2O$, 11 g of $NiCl_2.6H_2O$, 13.8 g of $FeSO_4.7H_2O$, 8.5 g of $MnSO_4.H_2O$, and 3.0 g of citric acid per liter. Samples are taken at various intervals and centrifuged. The supernatants are diluted and assayed using ABTS as a substrate.

Laccase activity is determined by syringaldazine oxidation. Specifically, 60 μl of syringaldazine stock solution (0.28 mM in 50% ethanol) and 20 μl of laccase sample are mixed with 0.8 ml of preheated Britton-Robinson buffer solution and incubated at 20° C. The oxidation is monitored at 530 nm over 5 minutes and activity is expressed as "SOU" μmole syringaldazine oxidized per minute ("SOU"). Britton-Robinson buffers with various pHs are used. ABTS oxidation assays are performed at 20° C. using 1 mM ABTS, Britton-Robinson buffers (diluted 1.1-fold) by monitoring $\Delta A405$ in 96-well plates.

For pDSY67, 3, 8, and 64 transformants, which are positive on ABTS, are obtained in *Aspergillus oryzae* JeRS316, JeRS317, and HowB712, respectively. For pDSY68, 34 and 56 transformants, which are positive on ABTS plates, are obtained in JeRS317 and HowB712, respectively. On average >90% of the primary transformants are positive on ABTS plates. All of the transformants are spore purified and tested in shake flask for production of the laccase as described above. Laccase activity assays confirm that the transformants, which are positive on ABTS plates, are indeed producing laccase.

Example 15
Purification and characterization of recombinant *Coprinus cinereus* Lcc1

*Aspergillus oryzae* JeRS317 (pDSY68, lcc1) is inoculated into a 10 liter lab fermentor containing medium comprised of Nutriose, yeast extract, $(NH_4)_2HPO_4$, $MgSO_4.7H_2O$, citric acid, $K_2SO_4$, $CaCl_2.H_2O$, and trace metals solution and supplemented with $CuSO_4$ and fermented at 31° C., pH 7, 600–700 rpm for 7 days. The broth is then recovered and filtered through cheesecloth.

Cheesecloth filtered broth (pH 7.2, 15 mS) is filtered through Whatman #2 filter paper, then concentrated and washed on a Spiral Concentrator (Amicon) with a S1Y30 membrane (16-fold, 0.8 mS). The broth is frozen overnight at –20° C., thawed the next day, filtered again on Whatman #2 paper, and loaded onto a 120 ml Q-Sepharose XK26 column (Pharmacia, Uppsala, Sweden), pre-equilibrated with 10 mM Tris pH 7.7, 0.9 mS (Buffer A). After loading and washing with Buffer A, a linear gradient with Buffer B (Buffer A plus 2 M NaCl) is applied and the active fractions are eluted around 7% Buffer B. The active fractions are dialyzed in Buffer A and then loaded onto a 40 ml Mono-Q 16/10 (Pharmacia, Uppsala, Sweden) column, pre-equilibrated with Buffer A. The active fractions pass through the column.

The sequential ion-exchange chromatography on Q-Sepharose and Mono-Q yields a recombinant *Coprinus cinereus* laccase preparation with apparent homogeneity by SDS-PAGE analysis. An overall 64-fold purification and a recovery of 23% are achieved.

A molecular weight of 66 kDa for the recombinant laccase is observed by SDS-PAGE analysis, similar to that of wild type laccase. The difference between the observed molecular weight and that derived from the DNA sequence (56 kDa) suggests the laccase is 18% glycosylated. The chromatographic elution pattern of recombinant laccase is very close to that of the recombinant *Myceliophthora thermophila* laccase under the same conditions, where the recombinant *Coprinus cinereus* laccase has a similar pI to the pI of 4.2 for recombinant *Myceliophthora thermophila* laccase, which is also close to the pI of wild type *Coprinus cinereus* laccase (3.7–4.0).

Copper (Cu) titration of the purified recombinant laccase with 2,2'-biquinoline is carried out as described by Felsenfeld, 1960, *Archives of Biochemistry and Biophysics* 87: 247–251. Photometric titration with 2,2'-biquinoline gives a Cu to protein (subunit) stoichiometry of 3.4±0.2, indicating the four-Cu oxidase nature of recombinant *Coprinus cinereus* laccase.

The purified recombinant *Coprinus cinereus* laccase shows a UV-visible spectrum with two maxima at 278 and 614 nm. The ratio of absorbance at 280 nm to that at 600 nm is found as 22.

The extinction coefficient for the enzyme is determined by amino acid analysis and the molecular weight derived from the DNA sequence. Amino acid analysis suggests an extinction coefficient of 1.6 l/(g*cm), similar to the predicted value of 1.2.

The redox potential is measured by monitoring the recombinant *Coprinus cinereus* laccase's absorbance change at 600 nm with $K_3Fe(CN)_6$—$K_4Fe(CN)_6$ couple (0.433 V) and with $I_2$—NaI couple (0.536 V) in 9 mM MES-NaOH pH 5.3 buffer. At pH 5.3, a redox potential of 0.55±0.06 V is observed for the recombinant *Coprinus cinereus* laccase.

Figure 6A:
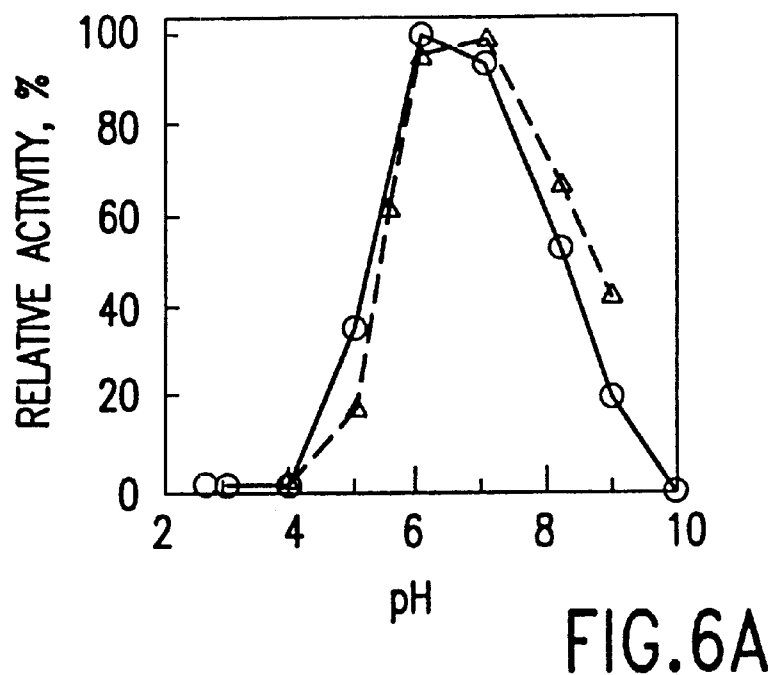
FIG. 6 illustrates the pH activity profiles of recombinant and wild-type *Coprinus cinereus* laccases using (A) syringaldazine and (B) of 2,2'-azinobis-(3-ethybenzthiazoline-6-sulfonic acid (ABTS) as substrates.
Figure 6B:
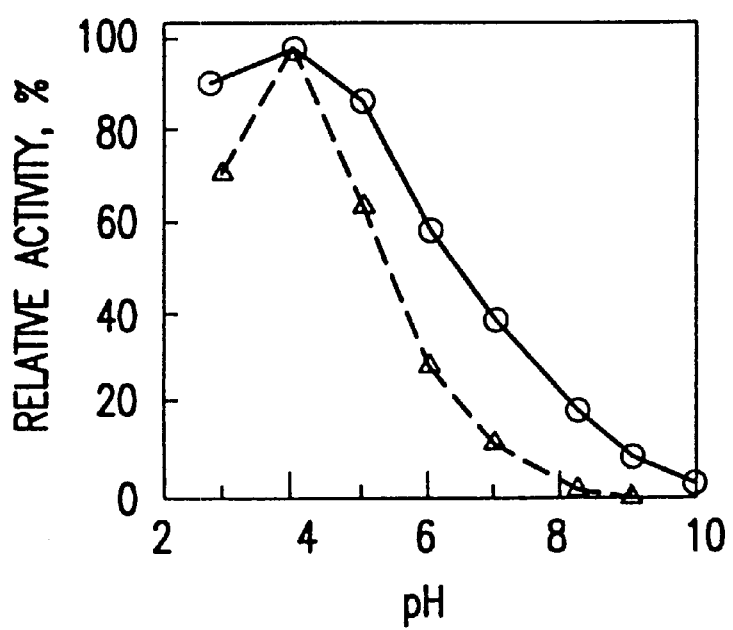

The activity of recombinant *Coprinus cinereus* laccase is tested with syringaldazine and ABTS. With syringaldazine as the substrate, recombinant Coprinus cinereus laccase shows a $LACU/A_{280}$ of 2.7 or a LACU/mg near 4. The recombinant laccase exhibits a pH activity profile in the pH range from about 4 to about 9 with optimal activity at pH 6 to 7 similar to that of wild type *Coprinus cinereus* laccase (FIG. 6A), at which its $SOU/A_{280}$=5.6. At pH 5.3, syringaldazine shows a $K_m$ of 26±6 μM and a $k_{cat}$ of 180±20 $min^{-1}$. With ABTS as the substrate, the recombinant laccase shows a pH activity profile in the pH range from about 2.7 to about 7 with optimal activity at pH 4 similar to wild type *Coprinus cinereus* laccase (FIG. 6B). At pH 5.3, a $K_m$ of 23±3 μM and a $k_{cat}$ of 1090±30 $min^{-1}$ are observed for ABTS oxidation. The values for $K_m$ and $k_{cat}$ are determined by fitting initial rates (v=$\Delta A/\Delta t/\Delta e$; $\Delta e$: extinction coefficient change), laccase concentration (E), and substrate concentration (S) into v=$k_{cat}$*E*S/($K_m$+S) with the Prizm nonlinear regression software (GraphPad, San Diego, Calif.). Total amino acid analysis, from which the extinction coefficient is determined, is performed on a HP AminoQuant instrument.

Example 16
N-terminal sequencing

Wild type Coprinus cinereus laccase is treated with a number of deblocking agents in order to remove the blocked N-terminus. Buffer exchange of samples is carried out in BioRad's BioSpin (P-6) device. Samples are treated with pyroglutamate aminopeptidase (Boehringer Mannheim, Indianapolis, Ind. and Sigma, St. Louis, Mo.), acylamino acid peptidase (Boehringer Mannheim, Indianapolis, Ind.), and acylase I (Sigma, St. Louis, Mo.) with deblocking protocols adapted from manufacturer's recommendations as follows. For pyroglutamate aminopeptidase treatment, a laccase sample is exchanged into 5% glycerol-10 mM EDTA-0.1 M sodium phosphate pH 8, then mixed with dithiothreitol (DTT) to 0.7 mM and horse liver peptidase (Sigma, St. Lois, Mo.) to 1/216 w/w laccase. The mixture (~6.2 mg/ml in laccase) is divided into three aliquots, of which one is adjusted 1 M urea and another is adjusted 0.5 M guanidine-HCl. Each sample is incubated at 4° C. for 16 hours. For acylamino acid peptidase, a laccase sample is exchanged into 0.2 M NH$_4$HCO$_3$ pH 7.8, then mixed with EDTA to 1 mM, 2-mercaptoethanol to 1 mM, and peptidase to ⅕ w/w laccase. The mixture (~14 mg/ml in laccase) is divided into three aliquots, of which one is adjusted 0.01% in SDS, one is adjusted 0.08 M in guanidine-HCl, and another is adjusted 0.7 M in urea. Each sample is incubated at 37° C. for 20 hours. For treatment with acylase I, a laccase sample is exchanged into 0.1 M sodium phosphate pH 7, then mixed with the acylase to ⅓ w/w of laccase. The mixture (~15 mg/ml in laccase) is incubated at 37° C. for 22 hours.

The enzyme-treated laccase samples are concentrated using Amicon's Microcon-10 devices. The concentrated samples are run on SDS PAGE and electroblotted onto a PVDF membrane of sequencing grade (Novex, San Diego, Calif.). The PVDF membrane is stained with Coommassie blue R-250 to visualize the treated laccase bands. The PVDF membrane is cut to isolate the pieces containing the individual bands. Several lanes are combined and subjected directly to N-terminal sequencing on an ABI 476 Sequencer using a blot cartridge and liquid TFA delivery.

The purified wild-type *Coprinus cinereus* laccase has a blocked N-terminus. However, treatment with both acylamino acid peptidase and acylase I leads to an identical sequenceable N-terminus. The resulting N-terminal sequence is shown below where it is uncertain whether S represents the actual N-terminus in the mature laccase, as, if this is the case, it would require an unexpected deacylase function by acylamino peptidase.

SVDTMTLTNANVSPDGFTRAGI (SEQ ID NO:36)

Under the conditions described, no deblocking is observed with pyroglutamate aminopeptidase.

Direct N-terminal sequencing of the recombinant *Coprinus cinereus* laccase yields a blocked N-terminus, likely due to the same acylation at a Ser as observed in the wild-type laccase.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
| --- | --- | --- |
| *E. coli* DH5α with pDSY71 (lcc2 partial cDNA in pCRII) | NRRL-B 21495 | August 18, 1995 |
| *E. coli* DH5α with pDSY72 (lcc3 partial cDNA in pCRII) | NRRL-B 21496 | August 18, 1995 |
| *E. coli* DH10B(ZL) with pDSY73 (lcc1 genomic clone in pZL) | NRRL-B 21497 | August 18, 1995 |
| *E. coli* DH5α with pDSY100 | NRRL B-21589 | June 21, 1996 |
| *E. coli* DH5α with pDSY105 | NRRL B-21602 | July 11, 1996 |

---

What is claimed is:

1. An isolated nucleic acid sequence encoding a polypeptide having laccase activity comprising the amino acid sequence of amino acids 23 to 543 of SEQ ID NO:27, amino acids 17 to 517 of SEQ ID NO:29, or amino acids 19 to 517 of SEQ ID NO:33.

2. The nucleic acid sequence of claim 1, wherein the nucleic acid sequence encodes a polypeptide comprising the amino acid sequence of amino acids 23 to 543 of SEQ ID NO:27.

3. The nucleic acid sequence of claim 2, wherein the nucleic acid sequence is the mature coding region of SEQ ID NO:26.

4. The nucleic acid sequence of claim 1, wherein the nucleic acid sequence encodes a polypeptide comprising the amino acid sequence of amino acids 17 to 517 of SEQ ID NO:29.

5. The nucleic acid sequence of claim 4, wherein the nucleic acid sequence is the mature coding region of SEQ ID NO:28.

6. The nucleic acid sequence of claim 1, wherein the nucleic acid sequence encodes a polypeptide comprising the amino acid sequence of amino acids 19 to 517 of SEQ ID NO:33.

7. The nucleic acid sequence of claim 6, wherein the nucleic acid sequence is the mature coding region of SEQ ID NO:32.

8. A nucleic acid construct comprising the nucleic acid sequence of claim 1 operably linked to one or more control sequences capable of directing the expression of the polypeptide in a suitable expression host.

9. A recombinant expression vector comprising the nucleic acid construct of claim 8, a promoter, and transcriptional and translational stop signals.

10. A recombinant host cell comprising the nucleic acid construct of claim 8.

11. An isolated nucleic acid sequence encoding a polypeptide having laccase activity having the nucleic acid sequence contained in pDSY73 which is contained in *Escherichia coli* NRRL B-21497, pDSY100 which is contained in *Escherichia coli* NRRL B-21589, or pDSY105 which is contained in *Escherichia coli* NRRL B-21602.

12. The isolated nucleic acid sequence of claim 11 having the nucleic acid sequence contained in pDSY73 which is contained in *Escherichia coli* NRRL B-21497.

13. The isolated nucleic acid sequence of claim 11 having the nucleic acid sequence contained in pDSY100 which is contained in *Escherichia coli* NRRL B-21589.

14. The isolated nucleic acid sequence of claim 11 having the nucleic acid sequence contained in pDSY105 which is contained in *Escherichia coli* NRRL B-21602.

15. A method for obtaining a nucleic acid sequence, comprising (a) hybridizing a DNA from a Coprinus strain under medium stringency conditions with (i) the mature coding region of SEQ ID NO:26, SEQ ID NO:28, or SEQ ID NO:32 or (ii) its complementary strand, wherein the medium stringency conditions are defined by prehybridization and hybridization at 42° C. in 5× SSPE, 0.3% SDS, 200 μg/ml sheared and denatured salmon sperm DNA, and 35% formamide, and wash conditions are defined at 60° C. for 30 minutes in 0.2× SSC, 0.1% SDS; and (b) isolating the nucleic acid sequence from the DNA.

16. The method of claim 15, wherein the DNA is obtained from *Coprinus cinereus*.

17. A method for producing a polypeptide having laccase activity, comprising: (A) cultivating a recombinant host cell under conditions conducive for production of the polypeptide, and (B) isolating the polypeptide; wherein the host cell comprises a nucleic acid sequence obtained by (a) hybridizing a DNA from a Coprinus strain under medium stringency conditions with (i) the mature coding region of SEQ ID NO:26, SEQ ID NO:28, or SEQ ID NO:32 or (ii) its complementary strand, wherein the medium stringency conditions are defined by prehybridization and hybridization at 42° C. in 5× SSPE, 0.3% SDS, 200 μg/ml sheared and denatured salmon sperm DNA, and 35% formamide, and wash conditions are defined at 60° C. for 30 minutes in 0.2× SSC, 0.1% SDS, and (b) isolating the nucleic acid sequence from the DNA.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 40 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Glu Val Asp Gly Gln Leu Thr Glu Pro His Thr Val Asp Arg Leu Gln
1               5                   10                  15

Ile Phe Thr Gly Gln Arg Tyr Ser Phe Val Leu Asp Ala Asn Gln Pro
            20                  25                  30

Val Asp Asn Tyr Trp Ile Arg Ala
            35                  40
```

(2) INFORMATION FOR SEQ ID NO:2:

(i) SEQUENCE CHARACTERISTICS:
      (A) LENGTH: 7 amino acids (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Xaa Xaa Asp Asn Pro Gly Pro
1               5

(2) INFORMATION FOR SEQ ID NO:3:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Phe Val Thr Asp Asn Pro Gly Pro
1               5

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Phe Val Thr Asp Asn Pro Gly Pro Trp
1               5

(2) INFORMATION FOR SEQ ID NO:5:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Ile Leu Asp Pro Ala Xaa Pro Gly Ile Pro Thr Pro Gly Ala Ala Asp
1               5                   10                  15
Val (2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Gly Val Leu Gly Asn Pro Gly Ile
1               5

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Xaa Phe Asp Asn Leu Thr Asn
1               5

(2) INFORMATION FOR SEQ ID NO:8:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Tyr Arg Xaa Arg Leu Ile Ser Leu Ser Cys Asn Pro Asp Trp Gln Phe
1               5                   10                  15

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Ala Asp Trp Tyr
1

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Ile Pro Ala Asp Pro Ser Ile Gln
1               5

(2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Glu Ser Pro Ser Val Pro Thr Leu Ile Arg Phe
1               5                   10

(2) INFORMATION FOR SEQ ID NO:12:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Ala Gly Thr Phe
1

(2) INFORMATION FOR SEQ ID NO:13:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Ser Gly Ala Gln Ser Ala Asn Asp Leu Leu Pro Ala Gly
1               5                   10

(2) INFORMATION FOR SEQ ID NO:14:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Ile Pro Ala Pro Ser Ile Gln Gly Ala Ala Gln Pro Asx Ala Thr
1               5                   10                  15

(2) INFORMATION FOR SEQ ID NO:15:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

ATCANTGGCA NGGNTNT                                                         17

(2) INFORMATION FOR SEQ ID NO:16:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

ATCANTGGCA NGGTTNTTN                                                       19

(2) INFORMATION FOR SEQ ID NO:17:

(i) SEQUENCE CHARACTERISTICS:
            (A) LENGTH: 23 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

TCATNTGNCA NTGANNAACC AGG                                              23

(2) INFORMATION FOR SEQ ID NO:18:

(i) SEQUENCE CHARACTERISTICS:
            (A) LENGTH: 1176 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..1176

(xi) SEQUENCE DESCRIPTION: SEQ ID NO:18:

```
CAT TGG CAC GGT CTC TTC CAA CGA GGG ACC AAC TGG GCT GAT GGT GCA        48
His Trp His Gly Leu Phe Gln Arg Gly Thr Asn Trp Ala Asp Gly Ala
  1               5                  10                  15

GAT GGT GTC AAC CAG TGC CCG ATC TCT CCA GGC CAT GCT TTC CTC TAC        96
Asp Gly Val Asn Gln Cys Pro Ile Ser Pro Gly His Ala Phe Leu Tyr
             20                  25                  30

AAG TTC ACT CCA GCT GGC CAC GCT GGT ACT TTC TGG TAC CAT TCC CAC       144
Lys Phe Thr Pro Ala Gly His Ala Gly Thr Phe Trp Tyr His Ser His
         35                  40                  45

TTT GGC ACC CAA TAC TGC GAT GGT CTC CGT GGT CCA ATG GTC ATT TAC       192
Phe Gly Thr Gln Tyr Cys Asp Gly Leu Arg Gly Pro Met Val Ile Tyr
     50                  55                  60

GAC GAC AAT GAC CCA CAC GCT GCC CTC TAC GAC GAG GAT GAC GAG AAC       240
Asp Asp Asn Asp Pro His Ala Ala Leu Tyr Asp Glu Asp Asp Glu Asn
 65                  70                  75                  80

ACC ATC ATT ACC CTC GCC GAT TGG TAC CAT ATC CCC GCT CCC TCC ATT       288
Thr Ile Ile Thr Leu Ala Asp Trp Tyr His Ile Pro Ala Pro Ser Ile
                 85                  90                  95

CAG GGT GCT GCC CAG CCT GAC GCT ACG CTC ATC AAC GGT AAG GGT CGC       336
Gln Gly Ala Ala Gln Pro Asp Ala Thr Leu Ile Asn Gly Lys Gly Arg
            100                 105                 110

TAC GTG GGC GGC CCA GCT GCC GAG CTT TCG ATC GTC AAT GTC GAG CAA       384
Tyr Val Gly Gly Pro Ala Ala Glu Leu Ser Ile Val Asn Val Glu Gln
        115                 120                 125

GGG AAG AAG TAC CGA ATG CGT TTG ATC TCG CTG TCC TGC GAC CCC AAC       432
Gly Lys Lys Tyr Arg Met Arg Leu Ile Ser Leu Ser Cys Asp Pro Asn
    130                 135                 140

TGG CAG TTC TCC ATT GAC GGA CAT GAG TTG ACG ATC ATT GAA GTC GAT       480
Trp Gln Phe Ser Ile Asp Gly His Glu Leu Thr Ile Ile Glu Val Asp
145                 150                 155                 160

GGT CAG CTT ACT GAG CCG CAT ACG GTT GAT CGT CTC CAG ATC TTC ACT       528
Gly Gln Leu Thr Glu Pro His Thr Val Asp Arg Leu Gln Ile Phe Thr
                165                 170                 175

GGT CAA AGG TAC TCC TTC GTT CTC GAC GCC AAC CAG CCG GTG GAC AAC       576
Gly Gln Arg Tyr Ser Phe Val Leu Asp Ala Asn Gln Pro Val Asp Asn
            180                 185                 190

TAC TGG ATC CGT GCT CAA CCC AAC AAG GGT CGA AAC GGA CTT GCT GGT       624
Tyr Trp Ile Arg Ala Gln Pro Asn Lys Gly Arg Asn Gly Leu Ala Gly
        195                 200                 205

ACC TTC GCC AAC GGT GTC AAC TCG GCC ATC CTT CGC TAT GCC GGC GCT       672
```

```
Thr Phe Ala Asn Gly Val Asn Ser Ala Ile Leu Arg Tyr Ala Gly Ala
    210                 215                 220

GCC AAC GCT GAT CCA ACC ACC TCC GCC AAC CCC AAC CCC GCC CAA CTC      720
Ala Asn Ala Asp Pro Thr Thr Ser Ala Asn Pro Asn Pro Ala Gln Leu
225                 230                 235                 240

AAC GAA GCC GAC CTC CAT GCT CTC ATC GAC CCC GCT GCT CCC GGT ATC      768
Asn Glu Ala Asp Leu His Ala Leu Ile Asp Pro Ala Ala Pro Gly Ile
                245                 250                 255

CCC ACT CCG GGC GCT GCA GAC GTC AAC CTC CGA TTC CAA TTG GGC TTC      816
Pro Thr Pro Gly Ala Ala Asp Val Asn Leu Arg Phe Gln Leu Gly Phe
                260                 265                 270

AGC GGC GGT CGA TTC ACG ATT AAC GGA ACC GCA TAC GAG AGT CCA AGC      864
Ser Gly Gly Arg Phe Thr Ile Asn Gly Thr Ala Tyr Glu Ser Pro Ser
            275                 280                 285

GTT CCT ACG CTC TTG CAG ATT ATG AGT GGT GCG CAG AGT GCG AAC GAC      912
Val Pro Thr Leu Leu Gln Ile Met Ser Gly Ala Gln Ser Ala Asn Asp
        290                 295                 300

TTG CTC CCT GCT GGA TCG GTG TAT GAG TTG CCC AGG AAC CAA GTT GTT      960
Leu Leu Pro Ala Gly Ser Val Tyr Glu Leu Pro Arg Asn Gln Val Val
305                 310                 315                 320

GAG CTT GTT GTT CCT GCT GGT GTC CTC GGT GGT CCT CAT CCT TTC CAT     1008
Glu Leu Val Val Pro Ala Gly Val Leu Gly Gly Pro His Pro Phe His
                325                 330                 335

CTC CAC GGT CAT GCG TTC AGT GTC GTC AGG AGT GCA GGC AGC AGC ACC     1056
Leu His Gly His Ala Phe Ser Val Val Arg Ser Ala Gly Ser Ser Thr
                340                 345                 350

TAC AAC TTT GTC AAC CCC GTC AAG CGC GAT GTT GTT AGT CTT GGT GTT     1104
Tyr Asn Phe Val Asn Pro Val Lys Arg Asp Val Val Ser Leu Gly Val
            355                 360                 365

ACT GGA GAC GAA GTT ACC ATT CGA TTC GTC ACC GAT AAC CCA GGC CCG     1152
Thr Gly Asp Glu Val Thr Ile Arg Phe Val Thr Asp Asn Pro Gly Pro
370                 375                 380

TGG TTC TTC CAC TGC CAC ATT GAA                                     1176
Trp Phe Phe His Cys His Ile Glu
385                 390

(2) INFORMATION FOR SEQ ID NO:19:

(i) SEQUENCE CHARACTERISTICS:
        (A) LENGTH: 392 amino acids
        (B) TYPE: amino acid
        (D) TOPOLOGY: linear (ii) MOLECULE TYPE: protein (xi) SEQUENCE DESCRIPTION: SEQ ID NO:19:

His Trp His Gly Leu Phe Gln Arg Gly Thr Asn Trp Ala Asp Gly Ala
1               5                   10                  15

Asp Gly Val Asn Gln Cys Pro Ile Ser Pro Gly His Ala Phe Leu Tyr
            20                  25                  30

Lys Phe Thr Pro Ala Gly His Ala Gly Thr Phe Trp Tyr His Ser His
        35                  40                  45

Phe Gly Thr Gln Tyr Cys Asp Gly Leu Arg Gly Pro Met Val Ile Tyr
    50                  55                  60

Asp Asp Asn Asp Pro His Ala Ala Leu Tyr Asp Glu Asp Glu Asn
65              70                  75                  80

Thr Ile Ile Thr Leu Ala Asp Trp Tyr His Ile Pro Ala Pro Ser Ile
            85                  90                  95

Gln Gly Ala Ala Gln Pro Asp Ala Thr Leu Ile Asn Gly Lys Gly Arg
        100                 105                 110
```

```
Tyr Val Gly Gly Pro Ala Ala Glu Leu Ser Ile Val Asn Val Glu Gln
        115                 120                 125

Gly Lys Lys Tyr Arg Met Arg Leu Ile Ser Leu Ser Cys Asp Pro Asn
130                 135                 140

Trp Gln Phe Ser Ile Asp Gly His Glu Leu Thr Ile Ile Glu Val Asp
145                 150                 155                 160

Gly Gln Leu Thr Glu Pro His Thr Val Asp Arg Leu Gln Ile Phe Thr
                165                 170                 175

Gly Gln Arg Tyr Ser Phe Val Leu Asp Ala Asn Gln Pro Val Asp Asn
                180                 185                 190

Tyr Trp Ile Arg Ala Gln Pro Asn Lys Gly Arg Asn Gly Leu Ala Gly
            195                 200                 205

Thr Phe Ala Asn Gly Val Asn Ser Ala Ile Leu Arg Tyr Ala Gly Ala
        210                 215                 220

Ala Asn Ala Asp Pro Thr Thr Ser Ala Asn Pro Asn Pro Ala Gln Leu
225                 230                 235                 240

Asn Glu Ala Asp Leu His Ala Leu Ile Asp Pro Ala Ala Pro Gly Ile
                245                 250                 255

Pro Thr Pro Gly Ala Ala Asp Val Asn Leu Arg Phe Gln Leu Gly Phe
                260                 265                 270

Ser Gly Gly Arg Phe Thr Ile Asn Gly Thr Ala Tyr Glu Ser Pro Ser
            275                 280                 285

Val Pro Thr Leu Leu Gln Ile Met Ser Gly Ala Gln Ser Ala Asn Asp
        290                 295                 300

Leu Leu Pro Ala Gly Ser Val Tyr Glu Leu Pro Arg Asn Gln Val Val
305                 310                 315                 320

Glu Leu Val Val Pro Ala Gly Val Leu Gly Pro His Pro Phe His
                325                 330                 335

Leu His Gly His Ala Phe Ser Val Val Arg Ser Ala Gly Ser Ser Thr
                340                 345                 350

Tyr Asn Phe Val Asn Pro Val Lys Arg Asp Val Val Ser Leu Gly Val
            355                 360                 365

Thr Gly Asp Glu Val Thr Ile Arg Phe Val Thr Asp Asn Pro Gly Pro
        370                 375                 380

Trp Phe Phe His Cys His Ile Glu
385                 390

(2) INFORMATION FOR SEQ ID NO:20:

(i) SEQUENCE CHARACTERISTICS:
        (A) LENGTH: 1170 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1170

(xi) SEQUENCE DESCRIPTION: SEQ ID NO:20:

CAC TGG CAC GGC ATG TTC CAA AGG GGG ACT GCC TGG GCT GAT GGT CCT      48
His Trp His Gly Met Phe Gln Arg Gly Thr Ala Trp Ala Asp Gly Pro
                395                 400                 405

GCT GGC GTC ACC CAA TGC CCT ATT TCC CCA GGG CAT TCG TTC TTG TAC      96
Ala Gly Val Thr Gln Cys Pro Ile Ser Pro Gly His Ser Phe Leu Tyr
    410                 415                 420

AAG TTC CAG GCT CTT AAC CAA GCC GGT ACT TTC TGG TAC CAC TCC CAT     144
```

```
Lys Phe Gln Ala Leu Asn Gln Ala Gly Thr Phe Trp Tyr His Ser His
425                 430                 435                 440

CAC GAA TCG CAA TAT TGT GAC GGT TTG CGT GGG GCT ATG GTC GTA TAT      192
His Glu Ser Gln Tyr Cys Asp Gly Leu Arg Gly Ala Met Val Val Tyr
                    445                 450                 455

GAC CCA GTC GAC CCA CAT CGC AAC TTG TAT GAC ATT GAC AAC GAG GCC      240
Asp Pro Val Asp Pro His Arg Asn Leu Tyr Asp Ile Asp Asn Glu Ala
                460                 465                 470

ACG ATC ATT ACG CTC GCA GAC TGG TAT CAC GTC CCT GCT CCC TCT GCA      288
Thr Ile Ile Thr Leu Ala Asp Trp Tyr His Val Pro Ala Pro Ser Ala
            475                 480                 485

GGT CTC GTT CCC ACC CCA GAT TCC ACG CTT ATC AAC GGT AAG GGC CGG      336
Gly Leu Val Pro Thr Pro Asp Ser Thr Leu Ile Asn Gly Lys Gly Arg
        490                 495                 500

TAT GCT GGT GGC CCT ACC GTA CCT CTC GCG GTC ATT TCT GTA ACC CGA      384
Tyr Ala Gly Gly Pro Thr Val Pro Leu Ala Val Ile Ser Val Thr Arg
505                 510                 515                 520

AAC CGA CGA TAC CGG TTC CGC CTT GTT TCC CTT TCA TGC GAT CCT AAT      432
Asn Arg Arg Tyr Arg Phe Arg Leu Val Ser Leu Ser Cys Asp Pro Asn
                525                 530                 535

TAT GTA TTC TCT ATC GAT GGG CAT ACC ATG ACT GTT ATT GAG GTC GAC      480
Tyr Val Phe Ser Ile Asp Gly His Thr Met Thr Val Ile Glu Val Asp
                540                 545                 550

GGA GTT AAC GTC CAA CCT CTC GTT GTC GAC TCG ATC CAG ATC TTC GCA      528
Gly Val Asn Val Gln Pro Leu Val Val Asp Ser Ile Gln Ile Phe Ala
            555                 560                 565

GGT CAG CGC TAC TCG TTC GTT CTC AAC GCC AAC CGC CCC GTC GGC AAC      576
Gly Gln Arg Tyr Ser Phe Val Leu Asn Ala Asn Arg Pro Val Gly Asn
        570                 575                 580

TAC TGG GTG CGA GCC AAC CCC AAC ATC GGT ACT ACG GGC TTC GTC GGT      624
Tyr Trp Val Arg Ala Asn Pro Asn Ile Gly Thr Thr Gly Phe Val Gly
585                 590                 595                 600

GGA GTC AAT TCT GCG ATT CTG CGC TAT GTG GGC GCC TCC AAT ACA GAC      672
Gly Val Asn Ser Ala Ile Leu Arg Tyr Val Gly Ala Ser Asn Thr Asp
                605                 610                 615

CCC ACT ACC ACC CAA ACT CCT TTC AGC AAC CCT CTC CTT GAG ACC AAT      720
Pro Thr Thr Thr Gln Thr Pro Phe Ser Asn Pro Leu Leu Glu Thr Asn
                620                 625                 630

CTC CAC CCC TTG ACC AAC CCT GCT GCT CCT GGC TTG CCT ACC CCA GGT      768
Leu His Pro Leu Thr Asn Pro Ala Ala Pro Gly Leu Pro Thr Pro Gly
            635                 640                 645

GGC GTC GAC GTC GCG ATC AAC CTT AAC ACG GTA TTC GAT TTC AGT AGT      816
Gly Val Asp Val Ala Ile Asn Leu Asn Thr Val Phe Asp Phe Ser Ser
        650                 655                 660

CTC ACC TTC TCC GTT AAC GGA GCC ACT TTC CAT CAA CCG CCC GTC CCT      864
Leu Thr Phe Ser Val Asn Gly Ala Thr Phe His Gln Pro Pro Val Pro
665                 670                 675                 680

GTC TTG CTT CAG ATC ATG AGC GGT GCA CAG ACT GCC CAG CAG CTT CTT      912
Val Leu Leu Gln Ile Met Ser Gly Ala Gln Thr Ala Gln Gln Leu Leu
                685                 690                 695

CCC TCC GGT TCG GTC TAC GTC CTT CCC CGT AAC AAA GTC ATC GAG CTT      960
Pro Ser Gly Ser Val Tyr Val Leu Pro Arg Asn Lys Val Ile Glu Leu
                700                 705                 710

TCT ATG CCT GGA GGC TCC ACT GGC AGT CCC CAT CCC TTC CAT CTC CAC     1008
Ser Met Pro Gly Gly Ser Thr Gly Ser Pro His Pro Phe His Leu His
            715                 720                 725

GGT CAC GAA TTT GCT GTG GTG AGA AGC GCG GGG AGT TCG ACC TAC AAC     1056
Gly His Glu Phe Ala Val Val Arg Ser Ala Gly Ser Ser Thr Tyr Asn
        730                 735                 740

TTC GCG AAC CCG GTA CGC AGG GAT GTC GTG AGT GCC GGT GTT GCT GGT     1104
```

```
Phe Ala Asn Pro Val Arg Arg Asp Val Val Ser Ala Gly Val Ala Gly
745                 750                 755                 760

GAC AAC GTC ACC ATT CGA TTC CGT ACC GAT AAC CCT GGA CCA TGG ATT      1152
Asp Asn Val Thr Ile Arg Phe Arg Thr Asp Asn Pro Gly Pro Trp Ile
                765                 770                 775

CTC CAT TGC CAT ATC GAC                                              1170
Leu His Cys His Ile Asp
                780
```

(2) INFORMATION FOR SEQ ID NO:21:

(i) SEQUENCE CHARACTERISTICS:
        (A) LENGTH: 390 amino acids
        (B) TYPE: amino acid
        (D) TOPOLOGY: linear (ii) MOLECULE TYPE: protein (xi) SEQUENCE DESCRIPTION: SEQ ID NO:21:

```
His Trp His Gly Met Phe Gln Arg Gly Thr Ala Trp Ala Asp Gly Pro
 1               5                  10                  15

Ala Gly Val Thr Gln Cys Pro Ile Ser Pro Gly His Ser Phe Leu Tyr
                20                  25                  30

Lys Phe Gln Ala Leu Asn Gln Ala Gly Thr Phe Trp Tyr His Ser His
             35                  40                  45

His Glu Ser Gln Tyr Cys Asp Gly Leu Arg Gly Ala Met Val Val Tyr
 50                  55                  60

Asp Pro Val Asp Pro His Arg Asn Leu Tyr Asp Ile Asp Asn Glu Ala
 65                  70                  75                  80

Thr Ile Ile Thr Leu Ala Asp Trp Tyr His Val Pro Ala Pro Ser Ala
                 85                  90                  95

Gly Leu Val Pro Thr Pro Asp Ser Thr Leu Ile Asn Gly Lys Gly Arg
                100                 105                 110

Tyr Ala Gly Gly Pro Thr Val Pro Leu Ala Val Ile Ser Val Thr Arg
            115                 120                 125

Asn Arg Arg Tyr Arg Phe Arg Leu Val Ser Leu Ser Cys Asp Pro Asn
130                 135                 140

Tyr Val Phe Ser Ile Asp Gly His Thr Met Thr Val Ile Glu Val Asp
145                 150                 155                 160

Gly Val Asn Val Gln Pro Leu Val Val Asp Ser Ile Gln Ile Phe Ala
                165                 170                 175

Gly Gln Arg Tyr Ser Phe Val Leu Asn Ala Asn Arg Pro Val Gly Asn
            180                 185                 190

Tyr Trp Val Arg Ala Asn Pro Asn Ile Gly Thr Thr Gly Phe Val Gly
        195                 200                 205

Gly Val Asn Ser Ala Ile Leu Arg Tyr Val Gly Ala Ser Asn Thr Asp
210                 215                 220

Pro Thr Thr Thr Gln Thr Pro Phe Ser Asn Pro Leu Leu Glu Thr Asn
225                 230                 235                 240

Leu His Pro Leu Thr Asn Pro Ala Ala Pro Gly Leu Pro Thr Pro Gly
                245                 250                 255

Gly Val Asp Val Ala Ile Asn Leu Asn Thr Val Phe Asp Phe Ser Ser
            260                 265                 270

Leu Thr Phe Ser Val Asn Gly Ala Thr Phe His Gln Pro Pro Val Pro
        275                 280                 285

Val Leu Leu Gln Ile Met Ser Gly Ala Gln Thr Ala Gln Gln Leu Leu
290                 295                 300
```

```
Pro Ser Gly Ser Val Tyr Val Leu Pro Arg Asn Lys Val Ile Glu Leu
305                 310                 315                 320

Ser Met Pro Gly Gly Ser Thr Gly Ser Pro His Pro Phe His Leu His
            325                 330                 335

Gly His Glu Phe Ala Val Val Arg Ser Ala Gly Ser Ser Thr Tyr Asn
            340                 345                 350

Phe Ala Asn Pro Val Arg Arg Asp Val Val Ser Ala Gly Val Ala Gly
        355                 360                 365

Asp Asn Val Thr Ile Arg Phe Arg Thr Asp Asn Pro Gly Pro Trp Ile
370                 375                 380

Leu His Cys His Ile Asp
385                 390

(2) INFORMATION FOR SEQ ID NO:22:

(i) SEQUENCE CHARACTERISTICS:
        (A) LENGTH: 1161 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..1161

(xi) SEQUENCE DESCRIPTION: SEQ ID NO:22:
```

| | | | | | | | | | | | | | | | | |
|---|---|---|---|---|---|---|---|---|---|---|---|---|---|---|---|---|
| CAC | TGG | CAC | GGT | TTC | TTG | CAG | GAG | GGT | ACA | GCT | TGG | GCC | GAC | GGT | CCT | 48 |
| His | Trp | His | Gly | Phe | Leu | Gln | Glu | Gly | Thr | Ala | Trp | Ala | Asp | Gly | Pro | |
| | | | | 395 | | | | 400 | | | | 405 | | | | |
| GCG | GGT | GTT | ACT | CAA | TGC | CCC | ATT | GCC | CCT | GGT | CAC | TCT | TTC | CTC | TAT | 96 |
| Ala | Gly | Val | Thr | Gln | Cys | Pro | Ile | Ala | Pro | Gly | His | Ser | Phe | Leu | Tyr | |
| | | | 410 | | | | 415 | | | | 420 | | | | | |
| AAG | TTC | CAG | GCC | AAA | AAC | CAA | GCT | GGT | ACC | TTC | TGG | TAC | CAT | TCC | CAC | 144 |
| Lys | Phe | Gln | Ala | Lys | Asn | Gln | Ala | Gly | Thr | Phe | Trp | Tyr | His | Ser | His | |
| | | | 425 | | | | 430 | | | | | 435 | | | | |
| CAC | ATG | TCT | CAG | TAT | TGT | GAC | GGC | CTG | AGA | GGC | GTC | ATG | GTC | GTT | TAC | 192 |
| His | Met | Ser | Gln | Tyr | Cys | Asp | Gly | Leu | Arg | Gly | Val | Met | Val | Val | Tyr | |
| | | | 440 | | | | 445 | | | | 450 | | | | | |
| GAT | CCC | CTA | GAT | CCC | CAT | CGT | CAC | CTG | TAT | GAC | GTT | GAT | AAC | GAG | AAT | 240 |
| Asp | Pro | Leu | Asp | Pro | His | Arg | His | Leu | Tyr | Asp | Val | Asp | Asn | Glu | Asn | |
| 455 | | | | 460 | | | | 465 | | | | 470 | | | | |
| ACT | ATC | ATC | ACG | CTC | GCG | GAC | TGG | TAT | CAC | GAT | CCC | GCC | CCT | TCT | GCT | 288 |
| Thr | Ile | Ile | Thr | Leu | Ala | Asp | Trp | Tyr | His | Asp | Pro | Ala | Pro | Ser | Ala | |
| | | | | 475 | | | | 480 | | | | 485 | | | | |
| GGA | CTC | GTC | CCA | ACC | CCC | TGG | TCG | ACT | TTG | ATC | AAT | GGC | AAG | GGC | CGT | 336 |
| Gly | Leu | Val | Pro | Thr | Pro | Trp | Ser | Thr | Leu | Ile | Asn | Gly | Lys | Gly | Arg | |
| | | | 490 | | | | 495 | | | | 500 | | | | | |
| TAC | CCA | GGC | GGA | CCC | GTC | GTG | CCC | TTG | GCC | GTC | ATT | CAC | GTC | AGC | CGC | 384 |
| Tyr | Pro | Gly | Gly | Pro | Val | Val | Pro | Leu | Ala | Val | Ile | His | Val | Ser | Arg | |
| | | 505 | | | | 510 | | | | 515 | | | | | | |
| GGA | AAG | CGC | TAC | CGC | TTC | CGC | CTC | GTC | TCC | CTT | TCG | TGC | GAC | CCT | AAC | 432 |
| Gly | Lys | Arg | Tyr | Arg | Phe | Arg | Leu | Val | Ser | Leu | Ser | Cys | Asp | Pro | Asn | |
| | 520 | | | | 525 | | | | 530 | | | | | | | |
| TAT | GTA | TTC | TCT | ATT | GAC | GGT | CAC | ACC | ATG | ACG | GTC | ATT | GAA | GTC | GAT | 480 |
| Tyr | Val | Phe | Ser | Ile | Asp | Gly | His | Thr | Met | Thr | Val | Ile | Glu | Val | Asp | |
| 535 | | | | 540 | | | | 545 | | | | 550 | | | | |
| GGT | GTC | AAC | CAT | GAA | CCG | TTG | GTT | GTC | GAC | CAC | ATT | CAA | ATC | TTT | GCT | 528 |
| Gly | Val | Asn | His | Glu | Pro | Leu | Val | Val | Asp | His | Ile | Gln | Ile | Phe | Ala | |
| | | | 555 | | | | 560 | | | | 565 | | | | | |
| GGT | CAA | CGG | TAC | TCG | TTT | GTC | TTG | AAC | GCC | AAC | CGG | CCC | GTC | AAC | AAC | 576 |

```
Gly Gln Arg Tyr Ser Phe Val Leu Asn Ala Asn Arg Pro Val Asn Asn
            570                 575                 580

TAC TGG GTC AGG GCT AAC CCC AAC CTC GGC TCT GTC GGC TTC GGT GGC       624
Tyr Trp Val Arg Ala Asn Pro Asn Leu Gly Ser Val Gly Phe Gly Gly
            585                 590                 595

GGT ATT AAT TCC GCA ATT CTG CGA TAT GTT GGA GCT CCT GCC GTC GAC       672
Gly Ile Asn Ser Ala Ile Leu Arg Tyr Val Gly Ala Pro Ala Val Asp
        600                 605                 610

CCA ACC ACC TCC CAA TTG CCT TTC AGC AAC CCA CTC CTC GAG ACC AAC       720
Pro Thr Thr Ser Gln Leu Pro Phe Ser Asn Pro Leu Leu Glu Thr Asn
615                 620                 625                 630

TTG CAC CCT CTC GTA AAT CCT GCT GCA CCT GGC GGC CCT TCC CCC GGT       768
Leu His Pro Leu Val Asn Pro Ala Ala Pro Gly Gly Pro Ser Pro Gly
            635                 640                 645

GAC GTC GAT GTC GCC ATC AAC CTG GAT ATC TTG TTC GAC GTC TCA ATC       816
Asp Val Asp Val Ala Ile Asn Leu Asp Ile Leu Phe Asp Val Ser Ile
        650                 655                 660

CTC AAG TTC ACT GTC AAC GGT GCT ACC TTC GAT GAA CCA CCC GTT CCG       864
Leu Lys Phe Thr Val Asn Gly Ala Thr Phe Asp Glu Pro Pro Val Pro
            665                 670                 675

GTC CTT CTC CAG ATT TTG AGC GGT GCA CAT ACC GCC TCA TCT CTT CTC       912
Val Leu Leu Gln Ile Leu Ser Gly Ala His Thr Ala Ser Ser Leu Leu
        680                 685                 690

CCC TCT GGC AGC GTC TAC ACT CTT CCC CCT AAC AAG GTC ATT GAG CTC       960
Pro Ser Gly Ser Val Tyr Thr Leu Pro Pro Asn Lys Val Ile Glu Leu
695                 700                 705                 710

ACT ATT CCC GGT GGT GGT ATC GGT GCT CCT CAC CCC ATC CAT CTT CAC      1008
Thr Ile Pro Gly Gly Gly Ile Gly Ala Pro His Pro Ile His Leu His
            715                 720                 725

GGC CAT ACC TTC AAG GTT GTC CGT AGC GCA GGC AGC TCG ACT TAC AAC      1056
Gly His Thr Phe Lys Val Val Arg Ser Ala Gly Ser Ser Thr Tyr Asn
        730                 735                 740

TTC GTC AAT CCC GTT GAG CGA GAT GTT GTC AAC GTT GGT CAA GCT GGC      1104
Phe Val Asn Pro Val Glu Arg Asp Val Val Asn Val Gly Gln Ala Gly
            745                 750                 755

GAC AAT GTC ACC ATT CGA TTC GTC ACT GAT AAT GCT GGT CCC TGG ATT      1152
Asp Asn Val Thr Ile Arg Phe Val Thr Asp Asn Ala Gly Pro Trp Ile
760                 765                 770

CTT CAC TGC                                                          1161
Leu His Cys
775

(2) INFORMATION FOR SEQ ID NO:23:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:23:

His Trp His Gly Phe Leu Gln Glu Gly Thr Ala Trp Ala Asp Gly Pro
 1               5                  10                  15

Ala Gly Val Thr Gln Cys Pro Ile Ala Pro Gly His Ser Phe Leu Tyr
                20                  25                  30

Lys Phe Gln Ala Lys Asn Gln Ala Gly Thr Phe Trp Tyr His Ser His
            35                  40                  45

His Met Ser Gln Tyr Cys Asp Gly Leu Arg Gly Val Met Val Val Tyr
        50                  55                  60
```

```
Asp Pro Leu Asp Pro His Arg His Leu Tyr Asp Val Asp Asn Glu Asn
 65                  70                  75                  80

Thr Ile Ile Thr Leu Ala Asp Trp Tyr His Asp Pro Ala Pro Ser Ala
                 85                  90                  95

Gly Leu Val Pro Thr Pro Trp Ser Thr Leu Ile Asn Gly Lys Gly Arg
            100                 105                 110

Tyr Pro Gly Gly Pro Val Val Pro Leu Ala Val Ile His Val Ser Arg
        115                 120                 125

Gly Lys Arg Tyr Arg Phe Arg Leu Val Ser Leu Ser Cys Asp Pro Asn
    130                 135                 140

Tyr Val Phe Ser Ile Asp Gly His Thr Met Thr Val Ile Glu Val Asp
145                 150                 155                 160

Gly Val Asn His Glu Pro Leu Val Val Asp His Ile Gln Ile Phe Ala
                165                 170                 175

Gly Gln Arg Tyr Ser Phe Val Leu Asn Ala Asn Arg Pro Val Asn Asn
            180                 185                 190

Tyr Trp Val Arg Ala Asn Pro Asn Leu Gly Ser Val Gly Phe Gly Gly
        195                 200                 205

Gly Ile Asn Ser Ala Ile Leu Arg Tyr Val Gly Ala Pro Ala Val Asp
    210                 215                 220

Pro Thr Thr Ser Gln Leu Pro Phe Ser Asn Pro Leu Leu Glu Thr Asn
225                 230                 235                 240

Leu His Pro Leu Val Asn Pro Ala Ala Pro Gly Gly Pro Ser Pro Gly
                245                 250                 255

Asp Val Asp Val Ala Ile Asn Leu Asp Ile Leu Phe Asp Val Ser Ile
            260                 265                 270

Leu Lys Phe Thr Val Asn Gly Ala Thr Phe Asp Glu Pro Pro Val Pro
    275                 280                 285

Val Leu Leu Gln Ile Leu Ser Gly Ala His Thr Ala Ser Ser Leu Leu
290                 295                 300

Pro Ser Gly Ser Val Tyr Thr Leu Pro Pro Asn Lys Val Ile Glu Leu
305                 310                 315                 320

Thr Ile Pro Gly Gly Gly Ile Gly Ala Pro His Pro Ile His Leu His
                325                 330                 335

Gly His Thr Phe Lys Val Val Arg Ser Ala Gly Ser Ser Thr Tyr Asn
            340                 345                 350

Phe Val Asn Pro Val Glu Arg Asp Val Val Asn Val Gly Gln Ala Gly
        355                 360                 365

Asp Asn Val Thr Ile Arg Phe Val Thr Asp Asn Ala Gly Pro Trp Ile
370                 375                 380

Leu His Cys
385
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ACTGCGATGG TCTCCGTGGT C                                            21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
GGGGCCTGGG TTATCGGTGA C                                            21
```

(2) INFORMATION FOR SEQ ID NO:26:

(i) SEQUENCE CHARACTERISTICS:
        (A) LENGTH: 3327 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(726..851, 907..1023, 1101..1247,
            1316..1696, 1752..2240, 2321..2494, 2548..2607,
            2670..2793)

(xi) SEQUENCE DESCRIPTION: SEQ ID NO:26:

```
CAACGTCAAA GGGCGAAAAA CCGTCTATCA GGGCGATGGC CCACTACGTG AACCATCACC    60

CTAATCAAGT TTTTTGGGGT CGAGGTGCCG TAAAGCACTA AATCGGAACC CTAAAGGGAG   120

CCCCCGATTT AGAGCTTGAC GGGGAAAGCC GGCGAACGTG GCGAGAAAGG AAGGGAAGAA   180

AGCGAAAGGA GCGGGCGCTA GGGCGCTGGC AAGTGTAGCG GTCACGCTGC GCGTAACCAC   240

CACACCCGCC GCGCTTAATG CGCCGCTACA GGGCGCGTCC CATTCGCCAT TCAGGCTGCG   300

CAACTGTTGG GAAGGGCGAT CGGTGCGGGC CTCTTCGCTA TTACGCCAGC TGGCGAAAGG   360

GGGATGTGCT GCAAGGCGAT TAAGTTGGGT AACGCCAGGG TTTTCCCAGT CACGACGTTG   420

TAAAACGACG GCCAGTGAAT TGAATTTAGG TGACACTATA GAAGAGCTAT GACGTCGCAT   480

GCACGCGTAC GTAAGCTTGG ATCCTCTAGA GCGACCGCCG ACTAGTGAGC TCGTCGACCC   540

GGGAATTGCA GCGTCCCTGG TCGTACGTTA GCCTACGCTT TACAGCACCG AAAGAAGTAT   600

AAAATCTGTA TGAAAGTTGG CGAAGAAACC TCAGACTACT CTCGTCGTCT ATCTTCACTC   660

CTCTGCTCCT CTCCTCCA CAGACTCTCC TTGACAGCCT CGTCGTATCA GAGAACAGAA     720
```

CAACA ATG TTC AAG AAC CTC CTC TCG TTC GCC CTT CTG GCG ATT AGC    767
          Met Phe Lys Asn Leu Leu Ser Phe Ala Leu Leu Ala Ile Ser
           1           5              10

GTT GCC AAC GCT CAG ATC GTC AAT TCG GTC GAT ACC ATG ACC CTC ACC    815
Val Ala Asn Ala Gln Ile Val Asn Ser Val Asp Thr Met Thr Leu Thr
 15           20            25            30

AAC GCG AAC GTC AGT CCC GAC GGT TTC ACT CGA GCT GTAAGTATAG    861
Asn Ala Asn Val Ser Pro Asp Gly Phe Thr Arg Ala
         35           40

GTCTTCAGCA CACTGTTGAT TATCCATTAC TTACCAACTT AACAG GGT ATC CTC    915
                                                   Gly Ile Leu
                                                               45

GTC AAT GGA GTT CAT GGA CCT CTT ATT CGA GGT GGA AAG AAC GAC AAC    963
Val Asn Gly Val His Gly Pro Leu Ile Arg Gly Gly Lys Asn Asp Asn
           50                  55                  60

TTT GAG CTC AAC GTC GTT AAC GAC TTG GAC AAC CCC ACT ATG CTT CGG    1011
Phe Glu Leu Asn Val Val Asn Asp Leu Asp Asn Pro Thr Met Leu Arg
           65                  70                  75

```
CCT ACC AGT ATC GTGAGTTCTA CAGAAATAAA CACTGATCCA TCATGATCCA             1063
Pro Thr Ser Ile
        80

GAACACTGAC AACGTTCTGA TTTTGGTTTG CTTGTAG CAT TGG CAC GGT CTC TTC        1118
                                        His Trp His Gly Leu Phe
                                                            85

CAA CGA GGG ACC AAC TGG GCT GAT GGT GCA GAT GGT GTC AAC CAG TGC         1166
Gln Arg Gly Thr Asn Trp Ala Asp Gly Ala Asp Gly Val Asn Gln Cys
            90                  95                 100

CCG ATC TCT CCA GGC CAT GCT TTC CTC TAC AAG TTC ACT CCA GCT GGC         1214
Pro Ile Ser Pro Gly His Ala Phe Leu Tyr Lys Phe Thr Pro Ala Gly
        105                 110                 115

CAC GCT GGT ACT TTC TGG TAC CAT TCC CAC TTT GTAAGCCCGA CCCCCCGACT       1267
His Ala Gly Thr Phe Trp Tyr His Ser His Phe
120             125                 130

ATGATCATCT TGACTGGAGT CCTGATTGAT GTCCAACTAA TTTACTAG GGC ACC CAA        1324
                                                    Gly Thr Gln

TAC TGC GAT GGT CTC CGT GGT CCA ATG GTC ATT TAC GAC GAC AAT GAC         1372
Tyr Cys Asp Gly Leu Arg Gly Pro Met Val Ile Tyr Asp Asp Asn Asp
            135                 140                 145

CCA CAC GCT GCC CTC TAC GAC GAG GAT GAC GAG AAC ACC ATC ATT ACC         1420
Pro His Ala Ala Leu Tyr Asp Glu Asp Asp Glu Asn Thr Ile Ile Thr
150             155                 160                 165

CTC GCC GAT TGG TAC CAT ATC CCC GCT CCC TCC ATT CAG GGT GCT GCC         1468
Leu Ala Asp Trp Tyr His Ile Pro Ala Pro Ser Ile Gln Gly Ala Ala
                170                 175                 180

CAG CCT GAC GCT ACG CTC ATC AAC GGT AAG GGT CGC TAC GTG GGC GGC         1516
Gln Pro Asp Ala Thr Leu Ile Asn Gly Lys Gly Arg Tyr Val Gly Gly
            185                 190                 195

CCA GCT GCC GAG CTT TCG ATC GTC AAT GTC GAG CAA GGG AAG AAG TAC         1564
Pro Ala Ala Glu Leu Ser Ile Val Asn Val Glu Gln Gly Lys Lys Tyr
200             205                 210

CGA ATG CGT TTG ATC TCG CTG TCC TGC GAC CCC AAC TGG CAG TTC TCC         1612
Arg Met Arg Leu Ile Ser Leu Ser Cys Asp Pro Asn Trp Gln Phe Ser
            215                 220                 225

ATT GAC GGA CAT GAG TTG ACG ATC ATT GAA GTC GAT GGT CAG CTT ACT         1660
Ile Asp Gly His Glu Leu Thr Ile Ile Glu Val Asp Gly Gln Leu Thr
230             235                 240                 245

GAG CCG CAT ACG GTT GAT CGT CTC CAG ATC TTC ACT GTAAGCATTG              1706
Glu Pro His Thr Val Asp Arg Leu Gln Ile Phe Thr
                250                 255

AAATCGGTGT GTTTCCGTTG AGAAAGCACA CTCACCTTTA ATCAG GGT CAA AGG           1760
                                                  Gly Gln Arg
                                                          260

TAC TCC TTC GTT CTC GAC GCC AAC CAG CCG GTG GAC AAC TAC TGG ATC         1808
Tyr Ser Phe Val Leu Asp Ala Asn Gln Pro Val Asp Asn Tyr Trp Ile
            265                 270                 275

CGT GCT CAA CCC AAC AAG GGT CGA AAC GGA CTT GCT GGT ACC TTC GCC         1856
Arg Ala Gln Pro Asn Lys Gly Arg Asn Gly Leu Ala Gly Thr Phe Ala
                280                 285                 290

AAC GGT GTC AAC TCG GCC ATC CTT CGC TAT GCC GGC GCT GCC AAC GCT         1904
Asn Gly Val Asn Ser Ala Ile Leu Arg Tyr Ala Gly Ala Ala Asn Ala
            295                 300                 305

GAT CCA ACC ACC TCC GCC AAC CCC AAC CCC GCC CAA CTC AAC GAA GCC         1952
Asp Pro Thr Thr Ser Ala Asn Pro Asn Pro Ala Gln Leu Asn Glu Ala
310             315                 320

GAC CTC CAT GCT CTC ATC GAC CCC GCT GCT CCC GGT ATC CCC ACT CCG         2000
Asp Leu His Ala Leu Ile Asp Pro Ala Ala Pro Gly Ile Pro Thr Pro
325             330                 335                 340
```

```
GGC GCT GCA GAC GTC AAC CTC CGA TTC CAA TTG GGC TTC AGC GGC GGT      2048
Gly Ala Ala Asp Val Asn Leu Arg Phe Gln Leu Gly Phe Ser Gly Gly
                345                 350                 355

CGA TTC ACG ATT AAC GGA ACC GCA TAC GAG AGT CCA AGC GTT CCT ACG      2096
Arg Phe Thr Ile Asn Gly Thr Ala Tyr Glu Ser Pro Ser Val Pro Thr
                360                 365                 370

CTC TTG CAG ATT ATG AGT GGT GCG CAG AGT GCG AAC GAC TTG CTC CCT      2144
Leu Leu Gln Ile Met Ser Gly Ala Gln Ser Ala Asn Asp Leu Leu Pro
                375                 380                 385

GCT GGA TCG GTG TAT GAG TTG CCC AGG AAC CAA GTT GTT GAG CTT GTT      2192
Ala Gly Ser Val Tyr Glu Leu Pro Arg Asn Gln Val Val Glu Leu Val
                390                 395                 400

GTT CCT GCT GGT GTC CTC GGT GGT CCT CAT CCT TTC CAT CTC CAC GGT      2240
Val Pro Ala Gly Val Leu Gly Gly Pro His Pro Phe His Leu His Gly
405                 410                 415                 420

GTACGTCAAG TTTTCTTTTC TCTTCTTTTT TTCATGGGTG GTCAAGTGTA CATGAGCTTA    2300

CCAAGGATTG AATTGTGTAG CAT GCG TTC AGT GTC GTC AGG AGT GCA GGC        2350
               His Ala Phe Ser Val Val Arg Ser Ala Gly
                            425                 430

AGC AGC ACC TAC AAC TTT GTC AAC CCC GTC AAG CGC GAT GTT GTT AGT      2398
Ser Ser Thr Tyr Asn Phe Val Asn Pro Val Lys Arg Asp Val Val Ser
                435                 440                 445

CTT GGT GTT ACT GGA GAC GAA GTT ACC ATT CGA TTC GTC ACC GAT AAC      2446
Leu Gly Val Thr Gly Asp Glu Val Thr Ile Arg Phe Val Thr Asp Asn
                450                 455                 460

CCA GGC CCG TGG TTC TTC CAC TGC CAC ATT GAA TTC CAT CTC ATG AAC      2494
Pro Gly Pro Trp Phe Phe His Cys His Ile Glu Phe His Leu Met Asn
                465                 470                 475

GTAAGTCTTC ATATCCATCG TTGTATACTC CAGAGTCTAA CCCACCTCCA CAG GGC       2550
                                                           Gly

TTG GCG ATC GTC TTT GCT GAA GAC ATG GCG AAC ACG GTT GAT GCT AAC      2598
Leu Ala Ile Val Phe Ala Glu Asp Met Ala Asn Thr Val Asp Ala Asn
480                 485                 490                 495

AAC CCA CCT GTACGTCCCC TCCTATTGAC TCAAATACTA ATTTCCGAAG              2647
Asn Pro Pro

CTAACTTCGG CATCAATTAC AG GTC GAG TGG GCC CAG CTT TGC GAG ATT TAC     2699
                        Val Glu Trp Ala Gln Leu Cys Glu Ile Tyr
                                    500                 505

GAT GAC CTG CCG CCT GAG GCG ACC TCG ATT CAA ACC GTT GTG CGT CGC      2747
Asp Asp Leu Pro Pro Glu Ala Thr Ser Ile Gln Thr Val Val Arg Arg
510                 515                 520

GCT GAG CCC ACC GGC TTT TCG GCC AAG TTC CGC AGG GAG GGC TTG          2792
Ala Glu Pro Thr Gly Phe Ser Ala Lys Phe Arg Arg Glu Gly Leu
525                 530                 535

TAGATAATAT TATAGTTGAC CAGAGGGCCA GTGGTAGGAG GCTGCTATAG TCAAAGTTGG    2852

TCACAGAGGG AAGAGTTAGT CGCAGAGAAG TCGTTTGAGT ACTACTAGTT ATTCATCGTG    2912

TTGTTATTTA TCGTGGTTGT TACATACTTA TTAACTATCG TTATGTGTGC TTGAGTTTGG    2972

AATGACAATG TATTTGATTG TCGAGTTGGA ATCCTTGTTG AAGTGCTAGT AACCTTTTGA    3032

TGGACCTCCG ACCTGCCTTT TCCCCGCACT TCCTCGATTG AATATTTGAG CGCGAGGCAC    3092

GAATCGAACC CACGACCCGC GAATGTCCAA ATTCCGGACC GGTACCTGCA GGCGTACCAG    3152

CTTTCCCTAT AGTGAGTCGT ATTAGAGCTT GGCGTAATCA TGGTCATAGC TGTTTCCTGT    3212

GTGAAATTGT TATCCGCTCA CAATTCCACA CAACATACGA GCCGGAAGCA TAAAGTGTAA    3272

AGCCTGGGGT GCCTAATGAG TGAGCTAACT CACATTAATT GCGTTGCGCT CACTG         3327

(2) INFORMATION FOR SEQ ID NO:27:
```

(i) SEQUENCE CHARACTERISTICS:
    (A) LENGTH: 539 amino acids
    (B) TYPE: amino acid
    (D) TOPOLOGY: linear (ii) MOLECULE TYPE: protein (xi) SEQUENCE DESCRIPTION: SEQ ID NO:27:

```
Met Phe Lys Asn Leu Leu Ser Phe Ala Leu Ala Ile Ser Val Ala
 1               5                  10                  15

Asn Ala Gln Ile Val Asn Ser Val Asp Thr Met Thr Leu Thr Asn Ala
                20                  25                  30

Asn Val Ser Pro Asp Gly Phe Thr Arg Ala Gly Ile Leu Val Asn Gly
             35                  40                  45

Val His Gly Pro Leu Ile Arg Gly Gly Lys Asn Asp Asn Phe Glu Leu
         50                  55                  60

Asn Val Val Asn Asp Leu Asp Asn Pro Thr Met Leu Arg Pro Thr Ser
 65                  70                  75                  80

Ile His Trp His Gly Leu Phe Gln Arg Gly Thr Asn Trp Ala Asp Gly
                 85                  90                  95

Ala Asp Gly Val Asn Gln Cys Pro Ile Ser Pro Gly His Ala Phe Leu
                100                 105                 110

Tyr Lys Phe Thr Pro Ala Gly His Ala Gly Thr Phe Trp Tyr His Ser
            115                 120                 125

His Phe Gly Thr Gln Tyr Cys Asp Gly Leu Arg Gly Pro Met Val Ile
        130                 135                 140

Tyr Asp Asp Asn Asp Pro His Ala Ala Leu Tyr Asp Glu Asp Asp Glu
145                 150                 155                 160

Asn Thr Ile Ile Thr Leu Ala Asp Trp Tyr His Ile Pro Ala Pro Ser
                165                 170                 175

Ile Gln Gly Ala Ala Gln Pro Asp Ala Thr Leu Ile Asn Gly Lys Gly
            180                 185                 190

Arg Tyr Val Gly Gly Pro Ala Ala Glu Leu Ser Ile Val Asn Val Glu
        195                 200                 205

Gln Gly Lys Lys Tyr Arg Met Arg Leu Ile Ser Leu Ser Cys Asp Pro
    210                 215                 220

Asn Trp Gln Phe Ser Ile Asp Gly His Glu Leu Thr Ile Ile Glu Val
225                 230                 235                 240

Asp Gly Gln Leu Thr Glu Pro His Thr Val Asp Arg Leu Gln Ile Phe
                245                 250                 255

Thr Gly Gln Arg Tyr Ser Phe Val Leu Asp Ala Asn Gln Pro Val Asp
            260                 265                 270

Asn Tyr Trp Ile Arg Ala Gln Pro Asn Lys Gly Arg Asn Gly Leu Ala
        275                 280                 285

Gly Thr Phe Ala Asn Gly Val Asn Ser Ala Ile Leu Arg Tyr Ala Gly
    290                 295                 300

Ala Ala Asn Ala Asp Pro Thr Thr Ser Ala Asn Pro Asn Pro Ala Gln
305                 310                 315                 320

Leu Asn Glu Ala Asp Leu His Ala Leu Ile Asp Pro Ala Ala Pro Gly
                325                 330                 335

Ile Pro Thr Pro Gly Ala Ala Asp Val Asn Leu Arg Phe Gln Leu Gly
            340                 345                 350

Phe Ser Gly Gly Arg Phe Thr Ile Asn Gly Thr Ala Tyr Glu Ser Pro
        355                 360                 365
```

```
Ser Val Pro Thr Leu Leu Gln Ile Met Ser Gly Ala Gln Ser Ala Asn
    370                 375                 380

Asp Leu Leu Pro Ala Gly Ser Val Tyr Glu Leu Pro Arg Asn Gln Val
385                 390                 395                 400

Val Glu Leu Val Val Pro Ala Gly Val Leu Gly Gly Pro His Pro Phe
                405                 410                 415

His Leu His Gly His Ala Phe Ser Val Val Arg Ser Ala Gly Ser Ser
                420                 425                 430

Thr Tyr Asn Phe Val Asn Pro Val Lys Arg Asp Val Val Ser Leu Gly
                435                 440                 445

Val Thr Gly Asp Glu Val Thr Ile Arg Phe Val Thr Asp Asn Pro Gly
                450                 455                 460

Pro Trp Phe Phe His Cys His Ile Glu Phe His Leu Met Asn Gly Leu
465                 470                 475                 480

Ala Ile Val Phe Ala Glu Asp Met Ala Asn Thr Val Asp Ala Asn Asn
                485                 490                 495

Pro Pro Val Glu Trp Ala Gln Leu Cys Glu Ile Tyr Asp Asp Leu Pro
                500                 505                 510

Pro Glu Ala Thr Ser Ile Gln Thr Val Val Arg Arg Ala Glu Pro Thr
                515                 520                 525

Gly Phe Ser Ala Lys Phe Arg Arg Glu Gly Leu
530                 535

(2) INFORMATION FOR SEQ ID NO:28:

(i) SEQUENCE CHARACTERISTICS:
        (A) LENGTH: 2940 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(588..704, 758..823, 877..945, 999..1145,
            1200..1271, 1324..1338, 1409..1438, 1488..1685,
            1749..2276, 2340..2360, 2413..2562, 2619..2642,
            2694..2750, 2804..2859)

(xi) SEQUENCE DESCRIPTION: SEQ ID NO:28:

ACTCACTATA GGGAAAGCTG GTACGCCTGC AGGTACCGGT CCGGAATTCC TTTCACCCCA     60

GATCCTGGTA TAGGATAGAC CCAGATACTC TTACTAAGGT GGCACGAATG ACCGACCGAA    120

TCTCGCGAGA AATCTTTCAA CTTTTCCAGA CACTTGATGA GTCGAAAACA ATGCGTTTAC    180

CCCTGGAGTT ACGGATTGGG TCTCAAGTGA CTGTTACAAC AAGCGCTCAG GATCCCCTAG    240

TATGTCTAAT CGTGACGTCT CTACCGACGC TTGGCGCTCA TTGACAGCTA TCGCGACAGA    300

TTCTTACATT TTTGTCAACG CCATCCTTTC TCGTTTACGT AGCTTTCTGC TACGGTGCTG    360

TCCTTTGTCA GAGATCCCTC CAGCACGACG ATTGATAACG AGATCTCAGT CGACGGAACG    420

GCTCCCTGGA CCTGATGCAC TTATCCTCTT ACTCATTGCA GTCATTACAA TCGAGTCTCG    480

TTCGCACGTT GTCACGGAAC GGGACCTGAA AAATGAAGGA TATAAACCCC CAAGTGCCGC    540

CCTGAAACTT TCAGACTTTT TGAGTCGACA AGCTCGAGGT CTCCAAC ATG CAA TTG      596
                                                   Met Gln Leu
                                                     1

CTT GCC TTC GTC CTC GCT GCT TTA CCC CTC GCA CGG GCT GCC ATT GGC      644
Leu Ala Phe Val Leu Ala Ala Leu Pro Leu Ala Arg Ala Ala Ile Gly
    5                  10                  15
```

```
CCT GTT GGC AAC CTA GTC ATC GCC AAC GCG AAC GTC TCA CCA GAC GGC          692
Pro Val Gly Asn Leu Val Ile Ala Asn Ala Asn Val Ser Pro Asp Gly
 20                  25                  30                  35

TTC GTT CGC TCG GTGAGTGGGC CGCGGCCTT TCACCATTTC TTTTCATTAA               744
Phe Val Arg Ser

CTCTCCTCTG CAG GCT GTC CTT GCC GGC GCT ACA GGT ACC AGC CTT GAG           793
               Ala Val Leu Ala Gly Ala Thr Gly Thr Ser Leu Glu
                40                  45                  50

CAC CCA GGG CCT GTT ATC GTG GGC CAG AAG GTAACACTAT TGACGTCCCT            843
His Pro Gly Pro Val Ile Val Gly Gln Lys
             55                  60

TGGTCAGAAT CCTTCCTTAC ACCCTTTATC TAG GGC GAC ACT TTC CAC ATC AAT         897
                                     Gly Asp Thr Phe His Ile Asn
                                                          65

GTC ATC GAT GAC CTT ACT GAC CCC ACT ATG CTT CGA ACA ACC AGT ATT          945
Val Ile Asp Asp Leu Thr Asp Pro Thr Met Leu Arg Thr Thr Ser Ile
 70                  75                  80

GTAAAGCAAA TTTGCTTGGC ATCCTTCAAA CTTCACACTG ACGTTCATGT CAG CAC           1001
                                                          His
                                                           85

TGG CAC GGT TTC TTG CAG GAG GGT ACA GCT TGG GCC GAC GGT CCT GCG          1049
Trp His Gly Phe Leu Gln Glu Gly Thr Ala Trp Ala Asp Gly Pro Ala
                 90                  95                  100

GGT GTT ACT CAA TGC CCC ATT GCC CCT GGT CAC TCT TTC CTC TAT AAG          1097
Gly Val Thr Gln Cys Pro Ile Ala Pro Gly His Ser Phe Leu Tyr Lys
                 105                 110                 115

TTC CAG GCC AAA AAC CAA GCT GGT ACC TTC TGG TAC CAT TCC CAC CAC          1145
Phe Gln Ala Lys Asn Gln Ala Gly Thr Phe Trp Tyr His Ser His His
                 120                 125                 130

GTGAGAGCGA TGCTGGTAAC GGACCTTGGG TCAATACTGA CTCTTGACTT ACAG ATG          1202
                                                            Met

TCT CAG TAT TGT GAC GGC CTG AGA GGC GTC ATG GTC GTT TAC GAT CCC          1250
Ser Gln Tyr Cys Asp Gly Leu Arg Gly Val Met Val Val Tyr Asp Pro
135                 140                 145                 150

CTA GAT CCC CAT CGT CAC CTG GTGCGTACGC CTATCTATGA CTCTCACCTT             1301
Leu Asp Pro His Arg His Leu
                 155

CGTACTCATT CCACCTACAC AG TAT GAC GTT GAT AAC GTAATCCTTC                  1348
                         Tyr Asp Val Asp Asn
                                      160

CAACCCTTAC GTCTCCGCTA AAGCTTACAT TCAATCTTCA TTGTTTCCTC ATTTTCTCAG        1408

GAG AAT ACT ATC ATC ACG CTC GCG GAC TGG GTAAGCGCGC AAATAACCTA            1458
Glu Asn Thr Ile Ile Thr Leu Ala Asp Trp
                 165                 170

CGAAAGTTCC AGTATCTGAC TGTTTTCAG TAT CAC GAT CCC GCC CCT TCT GCT          1511
                                Tyr His Asp Pro Ala Pro Ser Ala
                                              175             180

GGA CTC GTC CCA ACC CCC TGG TCG ACT TTG ATC AAT GGC AAG GGC CGT          1559
Gly Leu Val Pro Thr Pro Trp Ser Thr Leu Ile Asn Gly Lys Gly Arg
                 185                 190                 195

TAC CCA GGC GGA CCC GTC GTG CCC TTG GCC GTC ATT CAC GTC AGC CGC          1607
Tyr Pro Gly Gly Pro Val Val Pro Leu Ala Val Ile His Val Ser Arg
    200                 205                 210

GGA AAG CGC TAC CGC TTC CGC CTC GTC TCC CTT TCG TGC GAC CCT AAC          1655
Gly Lys Arg Tyr Arg Phe Arg Leu Val Ser Leu Ser Cys Asp Pro Asn
    215                 220                 225

TAT GTA TTC TCT ATT GAC GGT CAC ACC ATG GTTCGTAACC CTCCCATAAT            1705
Tyr Val Phe Ser Ile Asp Gly His Thr Met
    230                 235
```

```
CCACTCCTCC CCTGCCTCAT ATTTTACGTT TTGCGACTGT TAG ACG GTC ATT GAA          1760
                                                Thr Val Ile Glu
                                                        240

GTC GAT GGT GTC AAC CAT GAA CCG TTG GTT GTC GAC CAC ATT CAA ATC          1808
Val Asp Gly Val Asn His Glu Pro Leu Val Val Asp His Ile Gln Ile
            245                 250                 255

TTT GCT GGT CAA CGG TAC TCG TTT GTC TTG AAC GCC AAC CGG CCC GTC          1856
Phe Ala Gly Gln Arg Tyr Ser Phe Val Leu Asn Ala Asn Arg Pro Val
        260                 265                 270

AAC AAC TAC TGG GTC AGG GCT AAC CCC AAC CTC GGC TCT GTC GGC TTC          1904
Asn Asn Tyr Trp Val Arg Ala Asn Pro Asn Leu Gly Ser Val Gly Phe
275                 280                 285                 290

GGT GGC GGT ATT AAT TCC GCA ATT CTG CGA TAT GTT GGA GCT CCT GCC          1952
Gly Gly Gly Ile Asn Ser Ala Ile Leu Arg Tyr Val Gly Ala Pro Ala
                295                 300                 305

GTC GAC CCA ACC ACC TCC CAA TTG CCT TTC AGC AAC CCA CTC CTC GAG          2000
Val Asp Pro Thr Thr Ser Gln Leu Pro Phe Ser Asn Pro Leu Leu Glu
            310                 315                 320

ACC AAC TTG CAC CCT CTC GTA AAT CCT GCT GCA CCT GGC GGC CCT TCC          2048
Thr Asn Leu His Pro Leu Val Asn Pro Ala Ala Pro Gly Gly Pro Ser
        325                 330                 335

CCC GGT GAC GTC GAT GTC GCC ATC AAC CTG GAT ATC TTG TTC GAC GTC          2096
Pro Gly Asp Val Asp Val Ala Ile Asn Leu Asp Ile Leu Phe Asp Val
340                 345                 350

TCA ATC CTC AAG TTC ACT GTC AAC GGT GCT ACC TTC GAT GAA CCA CCC          2144
Ser Ile Leu Lys Phe Thr Val Asn Gly Ala Thr Phe Asp Glu Pro Pro
355                 360                 365                 370

GTT CCG GTC CTT CTC CAG ATT TTG AGC GGT GCA CAT ACC GCC TCA TCT          2192
Val Pro Val Leu Leu Gln Ile Leu Ser Gly Ala His Thr Ala Ser Ser
                375                 380                 385

CTT CTC CCC TCT GGC AGC GTC TAC ACT CTT CCC CCT AAC AAG GTC ATT          2240
Leu Leu Pro Ser Gly Ser Val Tyr Thr Leu Pro Pro Asn Lys Val Ile
            390                 395                 400

GAG CTC ACT ATT CCC GGT GGT GGT ATC GGT GCT CCT GTAGGTCTTT              2286
Glu Leu Thr Ile Pro Gly Gly Gly Ile Gly Ala Pro
        405                 410

CTTCTTCATC TTTCTCTCGA TCTCGATGGT GTTCACTCAC TATTTGAAAC CAG CAC           2342
                                                        His
                                                        415

CCC ATC CAT CTT CAC GGC GTGAGTATCC ATCCGTTAAG CTTCATTAAG                 2390
Pro Ile His Leu His Gly
            420

TCCCATGCTG ACCGTTTGAC AG CAT ACC TTC AAG GTT GTC CGT AGC GCA GGC         2442
                       His Thr Phe Lys Val Val Arg Ser Ala Gly
                                       425                 430

AGC TCG ACT TAC AAC TTC GTC AAT CCC GTT GAG CGA GAT GTT GTC AAC          2490
Ser Ser Thr Tyr Asn Phe Val Asn Pro Val Glu Arg Asp Val Val Asn
            435                 440                 445

GTT GGT CAA GCT GGC GAC AAT GTC ACC ATT CGA TTC GTC ACT GAT AAT          2538
Val Gly Gln Ala Gly Asp Asn Val Thr Ile Arg Phe Val Thr Asp Asn
        450                 455                 460

GCT GGT CCC TGG ATT CTT CAC TGC GTGCGCTATT TCTTTAGGCA TTCAACGTGT         2592
Ala Gly Pro Trp Ile Leu His Cys
465                 470

CAGAGTCTTA CCCCCGTTCT TTTCAG CAC ATT GAC TGG CAT TTG GTT TTG             2642
                           His Ile Asp Trp His Leu Val Leu
                                           475

GTAAGTTCAC GTTTTGACGC ATCAGGCGAA TGGTACTCTA ACTTCCTCCA G GGC CTG         2699
                                                        Gly Leu
                                                        480
```

```
TCT GTC GTC TTC GCG GAA GAT GTC CCC ACC ATC GAT AGC TCC GTT CAA        2747
Ser Val Val Phe Ala Glu Asp Val Pro Thr Ile Asp Ser Ser Val Gln
            485                 490                 495

CCT GTAAGTTCTG CGTGCCTCTG CTCGATATCA TTTGGCTGAC TTCTTGGCTT TAG         2803
Pro

CCC GCC TGG CAT GAT CTG TGC CCC ATC TAT GAC GCT CTT CCC CCC GGC        2851
Pro Ala Trp His Asp Leu Cys Pro Ile Tyr Asp Ala Leu Pro Pro Gly
500                 505                 510

ACG AGG TAATCTCGCC CATGACATAC TGGCACGGTA TGACTTGGAC AGGTTACGGA         2907
Thr Arg
515

AATCAAAGTA AATGTTGGAT AAGAAGAATA ACA                                   2940
```

(2) INFORMATION FOR SEQ ID NO:29:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO:29:

```
Met Gln Leu Leu Ala Phe Val Leu Ala Ala Leu Pro Leu Ala Arg Ala
 1               5                  10                  15

Ala Ile Gly Pro Val Gly Asn Leu Val Ile Ala Asn Ala Asn Val Ser
            20                  25                  30

Pro Asp Gly Phe Val Arg Ser Ala Val Leu Ala Gly Ala Thr Gly Thr
        35                  40                  45

Ser Leu Glu His Pro Gly Pro Val Ile Val Gly Gln Lys Gly Asp Thr
 50                  55                  60

Phe His Ile Asn Val Ile Asp Asp Leu Thr Asp Pro Thr Met Leu Arg
 65                  70                  75                  80

Thr Thr Ser Ile His Trp His Gly Phe Leu Gln Glu Gly Thr Ala Trp
                85                  90                  95

Ala Asp Gly Pro Ala Gly Val Thr Gln Cys Pro Ile Ala Pro Gly His
            100                 105                 110

Ser Phe Leu Tyr Lys Phe Gln Ala Lys Asn Gln Ala Gly Thr Phe Trp
        115                 120                 125

Tyr His Ser His His Met Ser Gln Tyr Cys Asp Gly Leu Arg Gly Val
    130                 135                 140

Met Val Val Tyr Asp Pro Leu Asp Pro His Arg His Leu Tyr Asp Val
145                 150                 155                 160

Asp Asn Glu Asn Thr Ile Ile Thr Leu Ala Asp Trp Tyr His Asp Pro
                165                 170                 175

Ala Pro Ser Ala Gly Leu Val Pro Thr Pro Trp Ser Thr Leu Ile Asn
            180                 185                 190

Gly Lys Gly Arg Tyr Pro Gly Gly Pro Val Val Pro Leu Ala Val Ile
        195                 200                 205

His Val Ser Arg Gly Lys Arg Tyr Arg Phe Arg Leu Val Ser Leu Ser
    210                 215                 220

Cys Asp Pro Asn Tyr Val Phe Ser Ile Asp Gly His Thr Met Thr Val
225                 230                 235                 240

Ile Glu Val Asp Gly Val Asn His Glu Pro Leu Val Val Asp His Ile
                245                 250                 255

Gln Ile Phe Ala Gly Gln Arg Tyr Ser Phe Val Leu Asn Ala Asn Arg
            260                 265                 270
```

Pro Val Asn Asn Tyr Trp Val Arg Ala Asn Pro Asn Leu Gly Ser Val
        275                 280                 285

Gly Phe Gly Gly Gly Ile Asn Ser Ala Ile Leu Arg Tyr Val Gly Ala
        290                 295                 300

Pro Ala Val Asp Pro Thr Thr Ser Gln Leu Pro Phe Ser Asn Pro Leu
305                 310                 315                 320

Leu Glu Thr Asn Leu His Pro Leu Val Asn Pro Ala Ala Pro Gly Gly
                325                 330                 335

Pro Ser Pro Gly Asp Val Asp Val Ala Ile Asn Leu Asp Ile Leu Phe
            340                 345                 350

Asp Val Ser Ile Leu Lys Phe Thr Val Asn Gly Ala Thr Phe Asp Glu
        355                 360                 365

Pro Pro Val Pro Val Leu Leu Gln Ile Leu Ser Gly Ala His Thr Ala
    370                 375                 380

Ser Ser Leu Leu Pro Ser Gly Ser Val Tyr Thr Leu Pro Pro Asn Lys
385                 390                 395                 400

Val Ile Glu Leu Thr Ile Pro Gly Gly Gly Ile Gly Ala Pro His Pro
                405                 410                 415

Ile His Leu His Gly His Thr Phe Lys Val Val Arg Ser Ala Gly Ser
            420                 425                 430

Ser Thr Tyr Asn Phe Val Asn Pro Val Glu Arg Asp Val Val Asn Val
        435                 440                 445

Gly Gln Ala Gly Asp Asn Val Thr Ile Arg Phe Val Thr Asp Asn Ala
450                 455                 460

Gly Pro Trp Ile Leu His Cys His Ile Asp Trp His Leu Val Leu Gly
465                 470                 475                 480

Leu Ser Val Val Phe Ala Glu Asp Val Pro Thr Ile Asp Ser Ser Val
                485                 490                 495

Gln Pro Pro Ala Trp His Asp Leu Cys Pro Ile Tyr Asp Ala Leu Pro
            500                 505                 510

Pro Gly Thr Arg
        515

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AGCTCGATGA CTTTGTTACG G                                        21

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CAGCGCTACT CGTTCGTTCT C                                        21

(2) INFORMATION FOR SEQ ID NO:32:

(i) SEQUENCE CHARACTERISTICS:
        (A) LENGTH: 3566 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(456..578, 631..696, 746..814, 869..1015,
            1069..1140, 1199..1213, 1271..1300, 1366..1563,
            1622..2149, 2213..2233, 2303..2452, 2514..2537,
            2598..2654, 2725..2776)

(xi) SEQUENCE DESCRIPTION: SEQ ID NO:32:

```
TGAAGGAGAA TCCCTCGAAG TGGAATTTTC TTTCCAGAAG ATGCAATCTG GTTTTGTCTC          60

ATCCATTTTT GTGACGTTTA CTCACCATTT CGAATCTAGG ATCGTTCGCC GATTTGCTCA         120

TATCTTTGCG ACCACTCAAT ATTGCTTTAC GTACCCCCTC GTGAGAGGCA CAAATGCATT         180

CCTTGCGATG CCCGATTCCA ATCTCAATGC AGGTACGTCC CTGGTTTCAT ACCAATGCGT         240

GTTTTGGACT GGCATTCCTG ACCTTTGTTC CGGTTGACGT TTCTAGTTAT TTCGTGTGAC         300

CTGTATGATT AATCGTACAG CCTGAATCTT GTCCTCAAAG TGCACAAATT AGGGCTCAAG         360

CTACCAGGCG AGGCAGGTAT AAAGCGCTCT ACTCTCCATC CGACGTTCCC CACTCACCAC         420

CAGCCGGCTG AGTTCACCCG TTCTTGAAAC TCGTT ATG TTG CTT TTA GCG ACT            473
                                      Met Leu Leu Leu Ala Thr
                                        1               5

GCT CTC GCT ACA TCC CTC TTA CCT TTC GTG CTG GGA GCC ATT GGC CCC           521
Ala Leu Ala Thr Ser Leu Leu Pro Phe Val Leu Gly Ala Ile Gly Pro
            10                  15                  20

AGT ACC AAC CTT GTC GTC GCG AAC AAG GTC ATC GCT CCC GAC GGC TTC           569
Ser Thr Asn Leu Val Val Ala Asn Lys Val Ile Ala Pro Asp Gly Phe
        25                  30                  35

AGT CGA TCT GTGAGCCTTT TCTGTGGACT GGACGCTTCT TCAGTGACTG                   618
Ser Arg Ser
    40

ATCATGTCGC AG GCT GTC CTC GCT GGC GCT ACC CAG CCA ACG GTG CAG             666
              Ala Val Leu Ala Gly Ala Thr Gln Pro Thr Val Gln
                                45                  50

TTC CCT GGC CCC GTC ATT CAA GGG AAT AAG GTAGGCAGAT TTCAACCGTT             716
Phe Pro Gly Pro Val Ile Gln Gly Asn Lys
            55                  60

TCCTGTCACA TCATGTTGAG TCTTTGTAG AAC AGT TTC TTT GCG ATC AAC GTC           769
                                Asn Ser Phe Phe Ala Ile Asn Val
                                                65              70

ATT GAC GCT CTG ACC GAC CCC ACT ATG CTG AGG ACT ACG AGT ATC               814
Ile Asp Ala Leu Thr Asp Pro Thr Met Leu Arg Thr Thr Ser Ile
        75                  80                  85

GTAAGTCAGT TCTATTGATG CTGCGATCAG CGGAAGCTCA CCATCTTTTA ACAG CAC           871
                                                              His

TGG CAC GGC ATG TTC CAA AGG GGG ACT GCC TGG GCT GAT GGT CCT GCT           919
Trp His Gly Met Phe Gln Arg Gly Thr Ala Trp Ala Asp Gly Pro Ala
        90                  95                  100

GGC GTC ACC CAA TGC CCT ATT TCC CCA GGG CAT TCG TTC TTG TAC AAG           967
Gly Val Thr Gln Cys Pro Ile Ser Pro Gly His Ser Phe Leu Tyr Lys
        105                 110                 115

TTC CAG GCT CTT AAC CAA GCC GGT ACT TTC TGG TAC CAC TCC CAT CAC          1015
Phe Gln Ala Leu Asn Gln Ala Gly Thr Phe Trp Tyr His Ser His His
120                 125                 130                 135

GTAACTACAA TCTATCTGTA CTGACGTGAC GATGTTGACT CAGTCATTCT CAG GAA           1071
```

```
                                              Glu
TCG CAA TAT TGT GAC GGT TTG CGT GGG GCT ATG GTC GTA TAT GAC CCA      11195
Ser Gln Tyr Cys Asp Gly Leu Arg Gly Ala Met Val Val Tyr Asp Pro
            140                 145                 150

GTC GAC CCA CAT CGC AAC TTG GTGAGCATCC TTTACTTTAT TCCCAAGGAA          1170
Val Asp Pro His Arg Asn Leu
        155

GCCATCAGTC TAATGACTTG CCATTTAG TAT GAC ATT GAC AAC GTATGTAACC         1223
                               Tyr Asp Ile Asp Asn
                                       160

TCCGGCGTTT GGTCGTCTTG TGATCCGCAG TTCACCTTGT TTTACAG GAG GCC ACG      1279
                                                    Glu Ala Thr
                                                            165

ATC ATT ACG CTC GCA GAC TGG GTAAGAATCT AATTACTTTC GATTACCTTC         1330
Ile Ile Thr Leu Ala Asp Trp
            170

GAGCATACCT AACTCGGGGC CCTTCTGTTC GCCAG TAT CAC GTC CCT GCT CCC       1383
                                      Tyr His Val Pro Ala Pro
                                              175             180

TCT GCA GGT CTC GTT CCC ACC CCA GAT TCC ACG CTT ATC AAC GGT AAG      1431
Ser Ala Gly Leu Val Pro Thr Pro Asp Ser Thr Leu Ile Asn Gly Lys
                185                 190                 195

GGC CGG TAT GCT GGT GGC CCT ACC GTA CCT CTC GCG GTC ATT TCT GTA      1479
Gly Arg Tyr Ala Gly Gly Pro Thr Val Pro Leu Ala Val Ile Ser Val
            200                 205                 210

ACC CGA AAC CGA CGA TAC CGG TTC CGC CTT GTT TCC CTT TCA TGC GAT      1527
Thr Arg Asn Arg Arg Tyr Arg Phe Arg Leu Val Ser Leu Ser Cys Asp
            215                 220                 225

CCT AAT TAT GTA TTC TCT ATC GAT GGG CAT ACC ATG GTACGCACTA           1573
Pro Asn Tyr Val Phe Ser Ile Asp Gly His Thr Met
        230                 235                 240

GTTCCCATCC CTGTAAAACG GGTGCTAACG ACGTGTATCA TCCCTTAG ACT GTT ATT     1630
                                                    Thr Val Ile

≥AG GTC GAC GGA GTT AAC GTC CAA CCT CTC GTT GTC GAC TCG ATC CAG      1678
Glu Val Asp Gly Val Asn Val Gln Pro Leu Val Val Asp Ser Ile Gln
            245                 250                 255

ATC TTC GCA GGT CAG CGC TAC TCG TTC GTT CTC AAC GCC AAC CGC CCC      1726
Ile Phe Ala Gly Gln Arg Tyr Ser Phe Val Leu Asn Ala Asn Arg Pro
260             265                 270                 275

GTC GGC AAC TAC TGG GTG CGA GCC AAC CCC AAC ATC GGT ACT ACG GGC      1774
Val Gly Asn Tyr Trp Val Arg Ala Asn Pro Asn Ile Gly Thr Thr Gly
            280                 285                 290

TTC GTC GGT GGA GTC AAT TCT GCG ATT CTG CGC TAT GTG GGC GCC TCC      1822
Phe Val Gly Gly Val Asn Ser Ala Ile Leu Arg Tyr Val Gly Ala Ser
            295                 300                 305

AAT ACA GAC CCC ACT ACC ACC CAA ACT CCT TTC AGC AAC CCT CTC CTT      1870
Asn Thr Asp Pro Thr Thr Thr Gln Thr Pro Phe Ser Asn Pro Leu Leu
            310                 315                 320

GAG ACC AAT CTC CAC CCC TTG ACC AAC CCT GCT GCT CCT GGC TTG CCT      1918
Glu Thr Asn Leu His Pro Leu Thr Asn Pro Ala Ala Pro Gly Leu Pro
            325                 330                 335

ACC CCA GGT GGC GTC GAC GTC GCG ATC AAC CTT AAC ACG GTA TTC GAT      1966
Thr Pro Gly Gly Val Asp Val Ala Ile Asn Leu Asn Thr Val Phe Asp
340             345                 350                 355

TTC AGT AGT CTC ACC TTC TCC GTT AAC GGA GCC ACT TTC CAT CAA CCG      2014
Phe Ser Ser Leu Thr Phe Ser Val Asn Gly Ala Thr Phe His Gln Pro
            360                 365                 370

CCC GTC CCT GTC TTG CTT CAG ATC ATG AGC GGT GCA CAG ACT GCC CAG      2062
Pro Val Pro Val Leu Leu Gln Ile Met Ser Gly Ala Gln Thr Ala Gln
            375                 380                 385
```

```
CAG CTT CTT CCC TCC GGT TCG GTC TAC GTC CTT CCC CGT AAC AAA GTC      2110
Gln Leu Leu Pro Ser Gly Ser Val Tyr Val Leu Pro Arg Asn Lys Val
        390                 395                 400

ATC GAG CTT TCT ATG CCT GGA GGC TCC ACT GGC AGT CCC GTAAGTCTTA        2159
Ile Glu Leu Ser Met Pro Gly Gly Ser Thr Gly Ser Pro
    405                 410                 415

ATTGTCTTCA TTTCCAACAA GTCGGTGATT AACGCTGGAT CATTCGCTGA CAG CAT        2215
                                                          His

CCC TTC CAT CTC CAC GGT GTATGTAGGC CTCTGTCTGA TCTCATTCGG              2263
Pro Phe His Leu His Gly
                420

AAGCGTTACT GACGGTGCTT CTTTGTTTCG ATCTGATAG CAC GAA TTT GCT GTG        2317
                                           His Glu Phe Ala Val
                                                           425

GTG AGA AGC GCG GGG AGT TCG ACC TAC AAC TTC GCG AAC CCG GTA CGC       2365
Val Arg Ser Ala Gly Ser Ser Thr Tyr Asn Phe Ala Asn Pro Val Arg
        430                 435                 440

AGG GAT GTC GTG AGT GCC GGT GTT GCT GGT GAC AAC GTC ACC ATT CGA       2413
Arg Asp Val Val Ser Ala Gly Val Ala Gly Asp Asn Val Thr Ile Arg
445                 450                 455                 460

TTC CGT ACC GAT AAC CCT GGA CCA TGG ATT CTC CAT TGC GTGCGTCAAG        2462
Phe Arg Thr Asp Asn Pro Gly Pro Trp Ile Leu His Cys
                465                 470

TCATCGTCCT CGTGCTGAAT TGATTGTCTA ACCAAGATAT CACATACTTA G CAT ATC      2519
                                                        His Ile
                                                            475

GAC TGG CAC CTT GTT TTG GTAAGTCTTC GCTTCTTCCA GACGTGATTA              2567
Asp Trp His Leu Val Leu
                480

ACTTTACTGA TCGCGATGAT GGGAATACAG GGG TTG GCT GTA GTG TTC GCT GAG      2621
                                 Gly Leu Ala Val Val Phe Ala Glu
                                                             485

GAC GCT CCT ACT GTT GCA ACC ATG GAT CCC CCT GTGAGTAGCG CCCGTGCTTT     2674
Asp Ala Pro Thr Val Ala Thr Met Asp Pro Pro
490                 495                 500

TGAGGAGTTG TGAAACCCGA GCTCAACGTG AAACGTTTTC CACTTTACAG CCT GCT        2730
                                                        Pro Ala

TGG GAC CAA CTT TGC CCG ATC TAC GAT GCT CTC CCT CCC AAC ACA           2775
Trp Asp Gln Leu Cys Pro Ile Tyr Asp Ala Leu Pro Pro Asn Thr
            505                 510                 515

TAAGTCGTTC AATTCAAGGC TGTTGACGTG AAGGGAGCAA GAAGGAAAGT AAGAGAAAGG     2835

CAGTCACATC CCGTCGGTTT GCCTCTGAAA TATCGATTAA TCACGCTTTT TATCACTTGT     2895

AATTATCTTT CTTTGTTACA GTGGCTCTTT GACGCTGGCT CTCCAGTGCG TTAGAGTCGA     2955

TAATAATAGC AATTCTCTAC TTTTAGGCAG ATTTTTAGGC AGGGCTGTGG TACGCTTTAT     3015

ATTAAGTTAA AAGAGCACCA ATAATGTCGC CCTCAGCTGG GCTCTTGTCG GCCGACTAGC     3075

TCAGTTGGTT AGAGCGTCGT GCTAATAACG CGAAGGTCTT GGGTTCGATC CCACGTTGG      3135

CCAGTAGCCC CCTTTTTGTT AATCCTGGCA CTTTCCTGTT CCTACTAACC CTTTTGAGAG     3195

TCCAGAAAAA TCACCATGAC TTAATTTTTT CTTTTCATAG AAGTCCTGGA AGGGTAAGGA     3255

AGTGATATAA CTAGATGACC CAACATTCAG TGCTGGTCGT CAGATGCAGG TGTCTTTTCG     3315

ACCAATCGAA GCATTCGGCG AAGATTCGAT CCAATTGCGC CTGCCTGTCC GCAGCATCTT     3375

CGAACGGCGA AGGACTGTCG AAGAACGTTA CGTACGCGCG GATTGTCAGT TTACGAAGGC     3435

GAGGAAACCC CATTGAGAGT AGATCGTCAA GCGTCTTCCA TTGGCCCAGG TCCACATTCA     3495
```

```
GATCGCAGCC GATTTGAACG ATAGGGATGA TATTGAGTCC TCCAGAACGT TCTGTCCCTG    3555

CATCAAAGCG A                                                         3566
```

(2) INFORMATION FOR SEQ ID NO:33:

(i) SEQUENCE CHARACTERISTICS:
        (A) LENGTH: 517 amino acids
        (B) TYPE: amino acid
        (D) TOPOLOGY: linear (ii) MOLECULE TYPE: protein (xi) SEQUENCE DESCRIPTION: SEQ ID NO:33:

```
Met Leu Leu Ala Thr Ala Leu Ala Thr Ser Leu Leu Pro Phe Val
 1               5                  10                  15

Leu Gly Ala Ile Gly Pro Ser Thr Asn Leu Val Ala Asn Lys Val
             20                  25                  30

Ile Ala Pro Asp Gly Phe Ser Arg Ser Ala Val Leu Ala Gly Ala Thr
         35                  40                  45

Gln Pro Thr Val Gln Phe Pro Gly Pro Val Ile Gln Gly Asn Lys Asn
     50                  55                  60

Ser Phe Phe Ala Ile Asn Val Ile Asp Ala Leu Thr Asp Pro Thr Met
 65                  70                  75                  80

Leu Arg Thr Thr Ser Ile His Trp His Gly Met Phe Gln Arg Gly Thr
                 85                  90                  95

Ala Trp Ala Asp Gly Pro Ala Gly Val Thr Gln Cys Pro Ile Ser Pro
            100                 105                 110

Gly His Ser Phe Leu Tyr Lys Phe Gln Ala Leu Asn Gln Ala Gly Thr
        115                 120                 125

Phe Trp Tyr His Ser His His Glu Ser Gln Tyr Cys Asp Gly Leu Arg
    130                 135                 140

Gly Ala Met Val Val Tyr Asp Pro Val Asp Pro His Arg Asn Leu Tyr
145                 150                 155                 160

Asp Ile Asp Asn Glu Ala Thr Ile Ile Thr Leu Ala Asp Trp Tyr His
                165                 170                 175

Val Pro Ala Pro Ser Ala Gly Leu Val Pro Thr Pro Asp Ser Thr Leu
            180                 185                 190

Ile Asn Gly Lys Gly Arg Tyr Ala Gly Gly Pro Thr Val Pro Leu Ala
        195                 200                 205

Val Ile Ser Val Thr Arg Asn Arg Arg Tyr Arg Phe Arg Leu Val Ser
    210                 215                 220

Leu Ser Cys Asp Pro Asn Tyr Val Phe Ser Ile Asp Gly His Thr Met
225                 230                 235                 240

Thr Val Ile Glu Val Asp Gly Val Asn Val Gln Pro Leu Val Val Asp
                245                 250                 255

Ser Ile Gln Ile Phe Ala Gly Gln Arg Tyr Ser Phe Val Leu Asn Ala
            260                 265                 270

Asn Arg Pro Val Gly Asn Tyr Trp Val Arg Ala Asn Pro Asn Ile Gly
        275                 280                 285

Thr Thr Gly Phe Val Gly Gly Val Asn Ser Ala Ile Leu Arg Tyr Val
    290                 295                 300

Gly Ala Ser Asn Thr Asp Pro Thr Thr Thr Gln Thr Pro Phe Ser Asn
305                 310                 315                 320

Pro Leu Leu Glu Thr Asn Leu His Pro Leu Thr Asn Pro Ala Ala Pro
                325                 330                 335
```

```
Gly Leu Pro Thr Pro Gly Gly Val Asp Val Ala Ile Asn Leu Asn Thr
        340             345             350

Val Phe Asp Phe Ser Ser Leu Thr Phe Ser Val Asn Gly Ala Thr Phe
        355             360             365

His Gln Pro Pro Val Pro Val Leu Leu Gln Ile Met Ser Gly Ala Gln
        370             375             380

Thr Ala Gln Gln Leu Leu Pro Ser Gly Ser Val Tyr Val Leu Pro Arg
385             390             395             400

Asn Lys Val Ile Glu Leu Ser Met Pro Gly Gly Ser Thr Gly Ser Pro
                405             410             415

His Pro Phe His Leu His Gly His Glu Phe Ala Val Val Arg Ser Ala
                420             425             430

Gly Ser Ser Thr Tyr Asn Phe Ala Asn Pro Val Arg Arg Asp Val Val
                435             440             445

Ser Ala Gly Val Ala Gly Asp Asn Val Thr Ile Arg Phe Arg Thr Asp
        450             455             460

Asn Pro Gly Pro Trp Ile Leu His Cys His Ile Asp Trp His Leu Val
465             470             475             480

Leu Gly Leu Ala Val Val Phe Ala Glu Asp Ala Pro Thr Val Ala Thr
                485             490             495

Met Asp Pro Pro Pro Ala Trp Asp Gln Leu Cys Pro Ile Tyr Asp Ala
        500             505             510

Leu Pro Pro Asn Thr
        515
```

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

AGAATTGACT CCACCGACGA A                                              21

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GAATTCTGGC ATTCCTGACC TTTGTTC                                    27

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Ser Val Asp Thr Met Thr Leu Thr Asn Ala Asn Val Ser Pro Asp Gly
1               5                   10                  15

Phe Thr Arg Ala Gly Ile
            20
```